United States Patent [19]

Cain et al.

[11] Patent Number: 5,169,855

[45] Date of Patent: Dec. 8, 1992

[54] PIPERIDINE ETHER DERIVATIVES AS PSYCHOTROPIC DRUGS OR PLANT FUNGICIDES

[75] Inventors: Gary A. Cain, New Castle; Paul J. Gilligan, Claymont; Sang W. Tam, Hockessin, all of Del.

[73] Assignee: Du Pont Merck Pharmaceutical Company, Wilmington, Del.

[21] Appl. No.: 506,961

[22] Filed: Mar. 28, 1990

[51] Int. Cl.$^5$ .................. A61K 31/445; C07D 211/22
[52] U.S. Cl. ........................... 514/319; 514/317; 514/331; 546/205; 546/232; 546/236; 546/240
[58] Field of Search ............... 546/14, 205, 206, 216, 546/232, 236; 514/317, 331, 319; 71/94

[56] References Cited

U.S. PATENT DOCUMENTS

| | | | |
|---|---|---|---|
| 3,360,526 | 12/1967 | Minor | 546/236 |
| 4,225,608 | 9/1980 | Uhl | 514/317 X |
| 4,508,724 | 4/1985 | Taylor et al. | 514/317 |
| 4,529,730 | 7/1985 | Schneider et al. | 514/319 |

FOREIGN PATENT DOCUMENTS

| | | | |
|---|---|---|---|
| 0004288 | 2/1979 | European Pat. Off. | 211/22 |
| 0190496 | 8/1986 | European Pat. Off. | 211/22 |
| 3614907 | 5/1987 | Fed. Rep. of Germany | 211/14 |
| 2514353 | 4/1983 | France | 546/216 |

OTHER PUBLICATIONS

Balsamo, et al., *J. Med. Chem.*, vol. 30, p. 222 (1987).

*Primary Examiner*—Robert W. Ramsuer
*Assistant Examiner*—Jacqueline Haley

[57] ABSTRACT

There are provided piperidine ether derivatives, pharmaceutical and agricultural compositions containing them useful for treating physiological or drug induced psychosis or dyskinesia in a mammal or fungal disease in plants. Also provided are methods for preparing these compounds.

21 Claims, No Drawings

PIPERIDINE ETHER DERIVATIVES AS PSYCHOTROPIC DRUGS OR PLANT FUNGICIDES

BACKGROUND OF INVENTION

1. Field of the Invention

This invention relates to disubstituted piperidine ether derivatives, pharmaceutical and agricultural compositions containing them and processes for preparing them and methods of using them as antipsychotics in mammals or as fungicides in plants.

2. Prior Art

The most relevant pharmaceutical references are included below. U.S. Pat. No. 4,508,724 (Taylor et al.) describes cardiac agents having the formula:

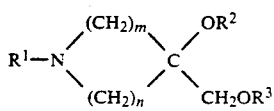

wherein
$R^1$ is hydrogen, loweralkyl or phenylloweralkyl;
$R^2$ is hydrogen, loweralkyl or acyl;
$R^3$ is phenyl, 1-naphthyl, 2-naphthyl, 1H-2,3-dihydroinden-4-yl and 1H-2,3-dihydroinden-5-yl;
m is 2 or 3; and
n is 1 or 2
with the proviso that m is never 3 when n is 2. These compounds are also disclosed as having antidepressant activity based on their ability to block the physiological effects of reserpine and related tetrabenzines which act primarily on serotonin.

U.S. Pat. No. 4,225,608 (Uhl et al.) describes antidepressant compounds of the formula:

wherein:
Ar is phenyl or phenyl which is monosubstituted or disubstituted by F, Cl, Br, alkyl or alkoxy each of 1-4 carbon atoms, cycloalkoxy of 3-6 carbon atoms, $CF_3$, CN, alkylthio of 1-4 carbon atoms, $SCF_3$, OH and/or alkanoyloxy of 1-10 carbon atoms;
R is $(1-R^1-2-\text{pyrrolidyl})-CH_2-CHR^2$, $(1-R^1-2-\text{piperidyl})-CH_2-CHR^2-$ or $1-R^1-3-Z-4-\text{hexahydroazepinyl}$;
$R^1$ is H, alkyl or alkenyl each of up to 4 carbon atoms, cyclopropylmethyl or benzyl;
$R^2$ is H, alkyl of 1-4 carbon atoms or phenyl; and
Z is alkyl of 1-4 carbon atoms;
with the proviso that Ar is p-fluorophenyl only when R is not 2-(1-methyl-2-piperidyl)-ethyl.

The antidepressant activity of the Uhl et al. compounds is related primarily to their reserpineantagonistic action.

Compounds useful as serotonin and noradrenaline uptake inhibitors, having the formula:

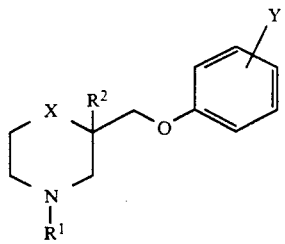

wherein:
$X = O$ or $CH_2$;
$R^1 = H$, alkyl, $CH_2Ph$ (when $R_2 = H$, $X = CH_2$, $Y = 2$-OEt);
$R^2 = H$, OH, $OCH_3$; and
$Y = H$, halogen, alkyl and alkoxy;
are described in Balsamo et al., J. Med. Chem., 30, 222 (1987). These compounds are weak antidepressants when $X = CH_2$.

EP 0,190,496 describes compounds of the formula:

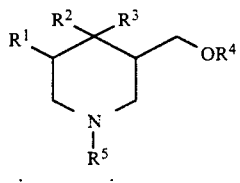

wherein:
$R^1$ and $R^2$ are H or form a bond;
$R^3$ and $R^4$ are independently optionally substituted phenyl or naphthyl; and
$R^5$ is $(CH_2)_nR^6$ where $n = 1$ or 2 and $R^6$ is optionally substituted phenyl or naphthyl.

These compounds are useful for the treatment of disorders related to gastrointestinal motility.

U.S. Pat. No. 3,360,526 discloses agricultural fungicidal compounds of the formula:

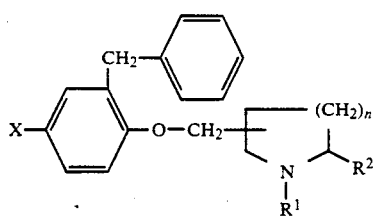

wherein:
X is H or chloro;
n is 1 or 2;
$R^1$ is (lower)alkyl; and
$R^2$ is hydrogen or methyl.

The preferred compounds of the reference are those compounds wherein the bond to the ethereal methylene group is located at the 3-position of the pyrrolidine ring and at the 3- or 4-position of the piperidine ring.

EP 004,288 describes 2-substituted piperidines exemplified by the following:

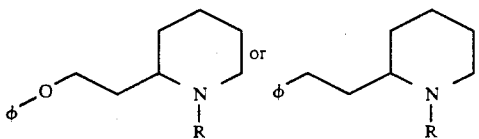

where R=H or Me.

In addition, DE 3,614,907 (BASF) describes compounds having fungicidal activity which are structurally similar to those of Formula (I) but which differ in that the bridge between the piperidine ring and Ar is at most one atom and contains only carbon.

None of the cited references nor any known reference suggest the novel compounds of this invention. Some of the compounds described in the prior art, cited above, are representative of antidepressant agents which characteristically exert their effect due to reserpineantagonistic activity.

Unlike the prior art antidepressant compounds, the compounds of the present invention are potent antipsychotic compounds which exert their effect through selective sigma receptor antagonism. Traditionally, antipsychotic agents such as the phenothiazines and butyrophenones have been potent dopamine receptor antagonists which are associated with a high incidence of side effects, particularly Parkinson-like motor effects or extra-pyramidal side effects (EPS) and dyskinesias including tardive dyskinesia at high doses. Many of these side effects are not reversible even after the dopamine receptor antagonist agent is discontinued.

The present invention is related to antipsychotic agents which are selective sigma receptor antagonists rather than the traditional dopamine receptor blockers known in the art, therefore, the compounds of the present invention have low potential for the typical movement disorders associated with dopamine antagonist antipsychotic agents while they maintain the ability to antagonize aggressive behavior and to antagonize hallucinogenic-induced behavior.

In addition the compounds of the present invention are useful for the control of fungal disease in plants

SUMMARY OF THE INVENTION

The compounds of the present invention are disubstituted piperidine ether derivatives of the formula:

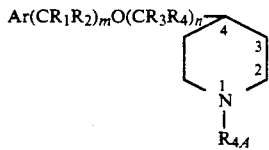

or a pharmaceutically or agriculturally acceptable salt thereof wherein:

$R_1$ to $R_4$ independently are H, alkyl of 1 to 3 carbon atoms or Ar";

Ar, Ar' and Ar" independently are phenyl groups optionally substituted with 1 to 5 substituents independently selected from the group consisting of:

H, halogen, OH, alkoxy of 1 to 4 carbon atoms, $NR_5R_6$, SH, $S(O)_qR_7$ where q=0,1,2, haloalkyl of 1 to 3 carbon atoms and 1 to 7 halogen atoms, alkyl of 1 to 4 carbon atoms, $CO_2H$, carboalkoxy of 2 to 6 carbon atoms, $CONR_8R_9$, CN, $NO_2$, $SO_2NR_{10}R_{11}$, $SO_3H$ or $OSiR_{12}R_{13}R_{14}$, or Ar and Ar' independently are naphthyl, pyridyl, pyrimidyl, quinolinyl, isoquinolinyl, dimethylisoxazolyl, thiazolyl, benzothiazolyl, fluorobenzothiazolyl, imidazolyl or benzimidazolyl each optionally substituted with 1 to 5 substituents independently selected from the group consisting of:

H, halogen, OH, alkoxy of 1 to 4 carbon atoms, $NR_5R_6$, SH, $S(O)_qR_7$ where q=0,1,2, haloalkyl of 1 to 3 carbon atoms and 1 to 7 halogen atoms, alkyl of 1 to 4 carbon atoms, $CO_2H$, carboalkoxy of 2 to 6 carbon atoms, $CONR_8R_9$, CN, $NO_2$, $SO_2NR_{10}R_{11}$, $SO_3H$ or $OSiR_{12}R_{13}R_{14}$;

$R_{4A}$ is $(CH_2)_pAr'$ (p is 1 to 3) or is selected from the group consisting of alkyl of 4 to 10 carbon atoms, alkenyl of 3 to 10 carbon atoms, alkynyl of 3 to 10 carbon atoms, cycloalkyl of 4 to 10 carbon atoms, cycloalkylalkyl of 4 to 10 carbon atoms or alkyl cycloalkyl of 4 to 10 carbon atoms, each optionally substituted with 1 to 3 substituents independently selected from the group consisting of:

7 5 halogen, hydroxyl, alkoxy of 1 to 6 carbon atoms, alkyl thio of 1 to 4 carbon atoms or Ar';

$R_5$–$R_{14}$ independently are H or alkyl of 1 to 4 carbon atoms;

m is 0 to 5; and n is 0 to 5; provided however that m and n cannot both be 0; provided that except as noted above, all other positions on the piperidine ring are substituted by hydrogen.

Preferred compounds of the present invention are those compounds of Formula (I) wherein:

$R_1$ to $R_4$ independently are H or methyl; and/or $R_{4A}$ is $(CH_2)_pAr'$, or alkyl of 4 to 10 carbon atoms, or alkylcycloalkyl of 4 to 8 carbon atoms; and/or Ar and Ar' independently are naphthyl, pyridyl, quinolinyl, isoquinolinyl, pyrimidyl, or phenyl each optionally substituted with 1 to 3 substituents as listed above; and/or m+n≦3; and/or p is 1 to 3.

More preferred compounds are those preferred compounds wherein:

$R_1$ to $R_4$ are H; and/or $R_4A$ is alkyl of 5 to 6 carbon atoms or $(CH_2)_pAr'$.

Specifically preferred compounds are as follows:

(a) 1-Benzyl-4-(2'(4"-fluorophenoxy)ethyl)piperidine, or the hydrochloride salt thereof;

(b) 1-Benzyl-4-(4'-fluorophenoxymethyl)piperidine, or the hydrochloride salt thereof;

(c) 1-Benzyl-4-(4'-chlorophenoxymethyl)piperidine, or the hydrochloride salt thereof;

(d) 1-(4'-Fluorobenzyl)-4-(4"-fluorophenoxymethyl)piperidine;

(e) 1-(2'-Naphthylmethyl)-4-(4"-fluorophenoxymethyl)piperidine;

(f) 1-Benzyl-4-(4'-trifluoromethyl)phenoxymethyl)piperidine, or the hydrochloride salt thereof;

(g) 1-(4'-Methoxybenzyl)-4-(4'-fluorophenoxymethyl)piperidine, or the maleate salt thereof;

(h) 1-(4'-Pyridylmethyl)-4-(4'-fluorophenoxymethyl)piperidine;

(i) 1-(4'-Chlorobenzyl)-4-(4'-fluorophenoxymethyl)piperidine, or the hydrochloride salt thereof;

(j) 1-Benzyl-(4'-nitrophenoxymethyl)piperidine, or the hydrochloride salt thereof;

(k) 1-Phenethyl-4-(4'-fluorobenzyloxymethyl)-piperidine, or the maleate salt thereof;

(l) 1-(2'-Pyridylmethyl)-4-(4''-fluorobenzyloxymethyl) piperidine, or the hydrochloride salt thereof; and (m) 1-(1'-Naphthylmethyl)-4-(4''-fluorobenzyloxymethyl)piperidine, or the hydrochloride salt thereof.

(n) 1-[(4-Chlorophenyl)methyl]-4-[[(4-fluorophenyl)methoxy]methyl]-piperidine.

(o) 1-[(Cyclohexyl)methyl-4-[[(4-fluorophenyl)methoxy]methyl]-piperidine.

(p) 4-[[4-[[(4-Fluorophenyl)methoxy]methyl]-1-piperidinyl]-methyl]phenol, or the hydrochloride salt thereof.

Compounds within the scope of this invention may have pharmaceutical utility, agriculture utility or both. Of the above listed specifically preferred compounds, compounds (a)-(m) or their salts are preferred for pharmaceutical uses and compounds (n)-(p) or their salts are preferred for agricultural uses.

Also provided are pharmaceutical compositions comprising a pharmaceutically acceptable carrier and an effective amount of a compound of Formula (I) or a pharmaceutically acceptable salt thereof and methods of treating physiological or drug induced psychosis or dyskinesia in a mammal comprising administering to the mammal an effective amount of a compound of the formula:

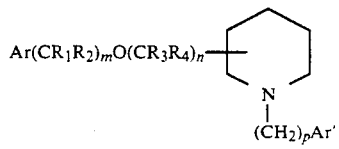

wherein:

$R_1$-$R_4$, m, n and p, Ar, Ar' and Ar'' are as defined above.

This invention further provides agricultural compositions comprising a compound of Formula (I) or its agriculturally suitable salt together with an agriculturally acceptable diluent or carrier and a method of controlling fungal diseases in plants.

Further provided are processes for the preparation of compounds of Formula (I) as set forth herein.

DETAILED DESCRIPTION OF THE INVENTION

The compounds of this invention wherein $R_{4A}$ is $(CH_2)_pAr'$ may be prepared by reacting compounds of Formula (III) and Formula (IV) in the presence of an azodicarboxylate ester (R=alkyl of 1 to 6 carbons) and a triarylphosphine in an inert solvent at reaction temperatures ranging from 0°-200° C., preferably 50° to 100° C. The choice of solvent and triarylphosphine will be apparent to those skilled in the art. In particular, the procedures described by O. Mitsunobu (*Synthesis*, p. 1 (1981)) are useful and relevant. The stoichiometry of reagents may vary depending on the reactivity of the substrates (III) and (IV). In general, a five to ten fold excess of azodicarboxylate and triarylphosphine gave optimal yields (Scheme I).

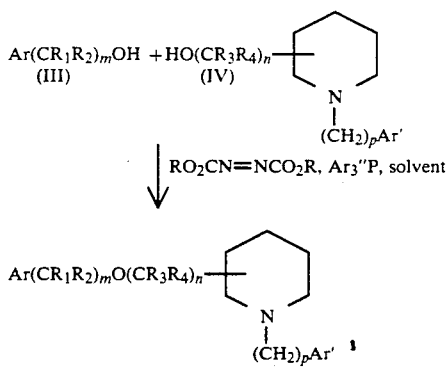

The compounds of this invention wherein $R_{4A}$ is $(CH_2)_pAr'$, may also be prepared by reacting an alcohol of Formula (VI) with a compound of Formula (V), where X is an appropriate leaving group, using a base and an inert solvent (Scheme II).

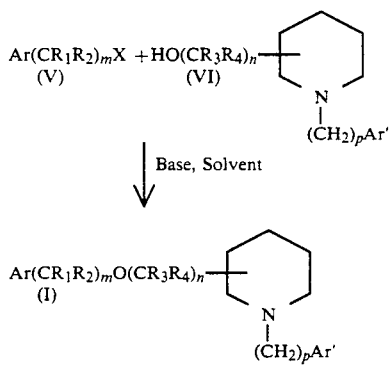

X may be halogen, sulfonate esters (preferably methanesulfonate or p-toluenesulfonate), phosphate esters or carboxylate esters such as acetate. Appropriate bases include but are not limited to alkali metal hydrides (preferably sodium hydride or potassium hydride), alkali metal amides (preferably lithium diisopropyl amide), alkali metal bis(trialkylsilylamides) (preferably lithium or potassium bis(trimethylsilyl) amides), trialkylamines, pyridine, quinoline, alkali metal carbonates, alkyl alkali metals (such as n-butyl lithium) or organo alkaline metal halides (such as arylmagnesium halides or alkylmagnesium halides). Inert solvents include ethereal solvents (such as dialkyl ethers or tetrahydrofuran or 1,2-dimethoxyethane), N,N-dialkyl formamides (preferably N,N-dimethylformamide), N,N'-dialkylacetamides, aromatic hydrocarbons (e.g., benzene, toluene, xylene), hydrocarbon solvents of 5 to 10 carbons, or alkanenitriles of 2 to 10 carbons (preferably acetonitrile). Reaction temperatures range from −80° C. to 200° C., preferably 0° C. to 80° C. The appropriate choice of base, solvent, leaving group X, and reaction solvent will be obvious to those skilled in the art. The examples taught by J. March (*Advanced Organic Chemistry* (3rd ed., (J. Wiley and Sons, New York, N.Y., 1985), pp 255-326)) are especially relevant.

SCHEME III

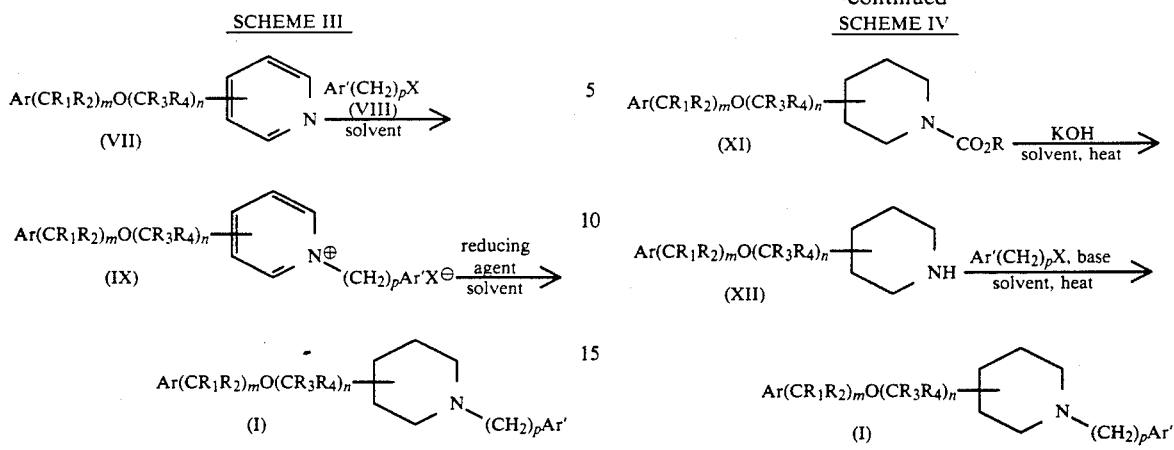

Compounds of this invention wherein $R_{4A}$ is $(CH_2)_p Ar'$ may also be prepared by Scheme III. A compound of Formula (VII) is reacted with a compound of Formula (VIII) where X is an appropriate leaving group as defined for Scheme II above. The reaction may be performed with or without an inert solvent. Inert solvents are the same as those defined for Scheme II. In addition, hydroxy hydrocarbons of 1 to 10 carbons (preferably methanol or ethanol or ethylene glycol) can be used. Reaction temperatures may range from 0° to 200° C. The starting pyridines (VII) may be prepared using the methods outlined for Scheme II employing an appropriate alcohol of Formula (III) and a pyridine of the Formula $X(CR_3R_4)_n\text{-}C_5H_5N$ or employing a compound of Formula (V) and a pyridine of the Formula $HO(CR_3R_4)_n\text{-}C_5H_5N$.

The pyridinium salts may be converted to the corresponding piperidines using a reducing agent in an inert solvent. Reducing agents include molecular hydrogen in the presence of a noble metal catalyst such as palladium on carbon, platinum on carbon, platinum dioxide or rhodium on alumina. Other reducing agents include alkali metal borohydrides (preferably sodium borohydride), diborane, alkali metal aluminum hydrides, trialkyltin hydrides, or diimide. Those skilled in the art will recognize that some of the above reagents will only partially reduce the pyridine ring to give tetrahydropyridine intermediates. It is therefore necessary to use combinations of the above reducing agents or to use these agents sequentially to afford the desired piperidine products. Inert solvents include those defined for Scheme II. In addition, hydroxy hydrocarbons of 1 to 10 carbons (preferably methanol or ethanol or ethylene glycol) can be used. The choice of reagents and solvents follow the examples taught by the March reference cited above (pp. 691–707, 1093–1120), and R. L. Augustine *Catalytic Hydrogenation*, (New York: Marcel Dekker, 1965).

SCHEME IV

-continued
SCHEME IV

The compounds of this invention wherein $R_{4A}$ is $(CH_2)_p Ar'$, may also be prepared according to Scheme IV. N-Benzylpiperidines of Formula (X) are reacted with an alkylchloroformate of 2 to 10 carbons in an inert solvent such as benzene, toluene or tetrahydrofuran at temperatures ranging from 25° C. to 120° C. to yield the corresponding carbamates.

Intermediates (XI) may be hydrolyzed to piperidines (XII) using an alkali metal hydroxide in water. Water miscible solvents may be used as co-solvents in cases where solubility is a problem. These water miscible solvents include hydroxy-hydrocarbons of 1 to 10 carbons (preferably methanol or ethanol), 1,4-dioxane or tetrahydrofuran. Reaction temperatures range from 25° C. to 150° C. The resulting piperidines (XII) may be reacted with a compound of the formula $Ar'(CH_2)_p X$ in the presence of a base and an inert solvent to yield compounds of Formula (I). X is a leaving group as defined for Scheme II. The same bases and inert solvents defined for Scheme II may be employed here.

SCHEME V

Some compounds of this invention wherein $R_{4A}$ is $(CH_2)_p Ar'$ may be prepared by reacting a compound of the formula ArX with a compound of Formula (IV) using a base and inert solvent (Scheme V). The definitions of X, base and inert solvent from Scheme II also apply here. Ar is preferably a p-nitrophenyl or a heteroaryl group.

SCHEME VI

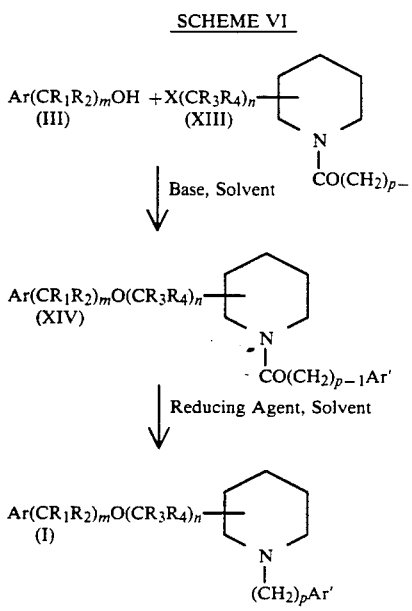

Alternatively compounds of this invention wherein $R_{4A}$ is $(CH_2)_p Ar'$, may be prepared by reacting a compound of Formula (III) with a compound of Formula (XIII) in the presence of a base in an inert solvent, as shown in Scheme VI. The definitions of X, base and solvent are the same as those used in Scheme II. The intermediates of Formula (XIV) may be treated with a reducing agent in an inert solvent to give compounds of Formula (I). Reducing agents and inert solvents are defined as for Scheme III.

All schemes (I-VI) can be used to make compounds of Formula (I) where $R_{4A}$ is alkyl. Compounds of Formula (I) wherein $R_{4A}$ is other than alkyl, for example alkenyl or alkynyl, can be made by Scheme IV.

Experimental Section

Analytical data were recorded for the compounds described below using the following general procedures. Infrared spectra were recorded on a Perkin-Elmer Model 1600 FT-IR spectrometer; absorbances are recorded in cm$^{-1}$ and intensities are denoted s (strong), m (moderate) and w (weak). Proton NMR spectra were recorded on an IBM-Bruker Model 200 FT-NMR (200 MHz); chemical shifts were recorded in parts per million (ppm) from an internal tetramethylsilane standard in deuterochloroform and coupling constants (J) are reported in Hz. Mass spectra (ms) or high resolution mass spectra (HRMS) were recorded on Finnegan MAT spectrometer. Melting points were recorded on a Buchi Model 510 melting point apparatus and are uncorrected. Boiling points are uncorrected. Parts and percentages are by weight unless otherwise indicated.

Reagents were purchased from commercial sources and, where necessary, purified prior to use according to the general procedures outlined by D. D. Perrin and W. L. F. Armarego, *Purification of Laboratory Chemicals*, 3rd ed., (New York: Pergamon Press, 1988). Chromatography was performed on silica gel using the solvent systems indicated below.

EXAMPLE 1

1-Benzyl-4-Carboethoxypiperidine

A mixture of ethyl isonipecotate (212 g, 1.35 mol), benzyl chloride (170 g, 1.35 mol) and potassium carbonate (322 g, 2.33 mol) in absolute ethanol (1.8 L) was stirred mechanically at room temperature for 72 h. Solvent was removed in vacuo and the residue was dissolved in water and then extracted with ether three times. The combined organic layers were dried over magnesium sulfate, filtered and solvent was removed in vacuo to give a pale yellow oil. Vacuum distillation (b.p. 134°-136° C., 1.0 Torr) gave a colorless liquid (252 g, 76% yield): $^1$H-NMR: 7.30-7.22 (m, 5H), 4.12 (q, 2H, J=7), 3.48 (s, 2H), 2.88-2.82 (m, 2H), 2.33-2.19 (m, 1H), 2.08-1.67 (m, 6H), 1.24 (t, 3H, J=7); Anal.: Calcd. for $C_{15}H_{21}NO_2$: C,72.84, H,8.56, N,5.66; Found: C,72.91, H,8.38, N,5.88.

EXAMPLES 2 TO 30B

Examples 2 to 30B were or could be prepared according to the procedure described for Example 1 using an appropriate organic halide. Reactions were conducted either at ambient or reflux temperatures.

TABLE 1

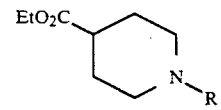

| Ex. No. | R | Notes |
|---|---|---|
| 1 | $C_6H_5CH_2$ | (a) |
| 2 | $4\text{-}(C_6H_5)C_6H_4CH_2$ | (b) |
| 3 | $3\text{-}(C_5H_4N)CH_2$ | (c) |
| 4 | $1\text{-}(C_{10}H_7)CH_2$ | (d) |
| 5 | $2\text{-}(C_{10}H_7)CH_2$ | (e) |
| 6 | $C_6H_5(CH_2)_2$ | (f) |
| 7 | $C_6H_5(CH_2)_3$ | (g) |
| 8 | $2\text{-}(C_5H_4N)CH_2$ | (h) |
| 9 | $4\text{-}(C_5H_4N)CH_2$ | (i) |
| 10 | $4\text{-}(C_4H_3N_2)CH_2$ | (j) |
| 11 | $2\text{-}(C_4H_3N_2)CH_2$ | |
| 12 | $6\text{-}(C_9H_7N)CH_2$ | (j) |
| 13 | $2\text{-}(C_9H_7N)CH_2$ | |
| 14 | $4\text{-F}\!-\!C_6H_4CH_2$ | |
| 15 | $4\text{-}CH_3O\!-\!C_6H_4\!-\!CH_2$ | |
| 16 | $4\text{-}PhCH_2OC_6H_4CH_2$ | |
| 17 | $3\text{-}PhCH_2OC_6H_4CH_2$ | |
| 18 | $4\text{-}ClC_6H_4CH_2$ | |
| 19 | $3\text{-}ClC_6H_4CH_2$ | |
| 20 | $4\text{-}(NO_2)C_6H_4CH_2$ | |
| 21 | $3\text{-}(NO_2)C_6H_4CH_2$ | |
| 22 | $3,4\text{-}(OCH_3)_2C_6H_3CH_2$ | |
| 23 | $3,4\text{-}F_2C_6H_3CH_2$ | |
| 24 | $3\text{-}(OCH_3)\text{-}4\text{-}BrC_6H_3CH_2$ | |
| 25 | $3,4\text{-}Cl_2C_6H_3CH_2$ | |
| 26 | $4\text{-}CH_3C_6H_4CH_2$ | |
| 27 | $4\text{-}(CO_2CH_3)C_6H_4CH_2$ | |
| 28 | $4\text{-}(SCH_3)C_6H_4CH_2$ | |
| 29 | $4\text{-}(SO_2CH_3)C_6H_4CH_2$ | |
| 30 | $4\text{-}(S(O)CH_3)C_6H_4CH_2$ | |
| 30A | $\underline{n}\text{-}C_6H_{13}$ | |

TABLE 1-continued

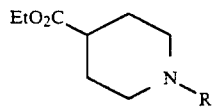

| Ex. No. | R | Notes |
|---|---|---|
| 30B | $C_6H_{11}CH_2$ | |

Notes:
(a) $^1$H-NMR: 7.30-7.22(m, 5H), 4.12(q, 2H, J=7), 3.48(s, 2H), 2.88-2.82(m, 2H), 2.33-2.19(m, 1H), 2.08-1.67(m, 6H), 1.24(t, 3H, J=7); Anal.: Calcd. for $C_{15}H_{21}NO_2$: C, 72.84, H, 8.56, N, 5.66; Found: C, 72.91, H, 8.38, N, 5.88.
(b) $^1$H-NMR: 7.60-7.23(m, 9H), 4.12(q, 2H, J=7), 3.52(s, 2H), 2.91-2.85(m, 2H), 2.34-1.74(m, 7H), 1.24(t, 3H, J=7); HR-MS: Calcd.: 323.1885; Found: 323.1882. b.p.(°C., (Torr))185-190(1.0); Anal. Calcd.: C, 77.98; H, 7.79; N, 4.43; Found: C, 78.74; H, 7.61; N, 4.07.
(c) b.p.(°C., (Torr))132-135(1.0)$^{(k)}$; Anal. Calcd.: C, 67.72; H, 8.12; N, 11.28; Found: C, 67.55; H, 8.28; N, 11.00.
(d) b.p.(°C., (Torr))175-183(0.9); Anal. Calcd.: C, 76.74; H, 7.80; N, 4.71; Found: C, 76.68; H, 7.83; N, 4.68.
(e) $^1$H-NMR: 7.82-7.71(m, 4H), 7.50-7.41(m, 3H), 4.11q, 2H, J=7), 3.62(s, 2H), 2.93-2.84(m, 2H), 2.28-1.74(m, 7H), 1.23(t, 3H, J=7); HR-MS: Calcd.: 297.1728; Found: 297.1730. b.p.(°C., (Torr))186-188(1.0); Anal. Calcd.: C, 76.74; H, 7.80; N, 4.71; Found: C, 74.68; H, 7.24; N, 5.00.
(f) b.p.(°C., (Torr))140-145(1.0)$^{(k)}$; Anal. Calcd.: C, 83.26; H, 8.78; N, 5.17; Found: C, 73.01; H, 8.77; N, 5.55.
(g) b.p.(°C., (Torr))160-164(1.6); Anal. Calcd.: C, 74.14; H, 9.15; N, 5.09; Found: C, 73.97; H, 9.07; N, 5.88.
(h) b.p.(°C., (Torr))138-140(0.8); Anal. Calcd.: C, 67.72; H, 8.12; N, 11.28; Found: C, 67.71; H, 8.19; N, 11.48.
(i) b.p.(°C., Torr))145-148(0.7); Anal. Calcd.: C, 67.72; H, 8.12; N, 11.28; Found: C, 67.74; H, 8.30; N, 11.24.
(j) $C_4H_3N_2$ = pyrimidyl, $C_9H_7N$ = quinolinyl.
(k) Kugelrohr oven temperature.

EXAMPLES 31 TO 43

Examples 31 to 43 were or could be prepared according to the procedure described for Example 1. Reactions were conducted either at room or reflux temperatures.

TABLE 2

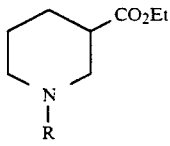

| Ex. No. | R | Notes |
|---|---|---|
| 31 | $C_6H_5CH_2$ | (a) |
| 32 | $3-(C_5H_4N)CH_2$ | |
| 33 | $4-(C_5H_4N)CH_2$ | |
| 34 | $2-(C_5H_4N)CH_2$ | |
| 35 | $2-(C_{10}H_7)CH_2$ | |
| 36 | $4-FC_6H_4CH_2$ | |
| 37 | $3-FC_6H_4CH_2$ | |
| 38 | $3-ClC_6H_4CH_2$ | |
| 39 | $4-ClC_6H_4CH_2$ | |
| 40 | $4-CH_3OC_6H_4CH_2$ | |
| 41 | $4-NO_2C_6H_4CH_2$ | |
| 42 | $4-CF_3C_6H_4CH_2$ | |
| 43 | $3-CF_3C_6H_4CH_2$ | |

Notes:
(a) Anal. Calcd.: C, 72.84; H, 87.56; N, 5.66; Found: C, 72.50; H, 8.61; N, 5.37.

EXAMPLE 44

Benzyl-b 4-(hydroxymethyl)piperidine

A suspension of lithium aluminum hydride (22.8 g, 0.6 mol) in anhydrous tetrahydrofuran (400 mL) was stirred mechanically at 0° C. under a nitrogen atmosphere. A solution of 1-benzyl-4-carboethoxypiperidine (26.5 g, 0.1 mol) in anhydrous tetrahydrofuran (400 mL) was added dropwise. After the addition was completed, the reaction mixture was heated to reflux temperature and stirred for 18 h. The reaction mixture was cooled to 0° C. and ethyl acetate (900 mL) was added dropwise. Water (23 mL), 2N sodium hydroxide solution (23 mL), then water (69 mL) were added with vigorous stirring. The inorganic salts were filtered and the filtrate was concentrated in Vacuo. Vacuum distillation (b.p. 140° C., 0.4 Torr) gave a clear, colorless liquid (12.5 g): $^1$H-NMR: 7.36-7.22 (m, 5H), 3.50 (s, 2H), 3.49 (dd, 2H, J=7,7), 2.94-2.86 (m, 2H), 2.02-1.17 (m, 8H); Anal.: Calcd. for $C_{13}H_{19}NO$: C,76.06, H,9.33, N,6.82; Found: C,75.87, H,9.16, N,6.55.

EXAMPLES 45 TO 67B

Examples 45 to 67B were or could be prepared according to the procedure described for Example 44.

TABLE 3

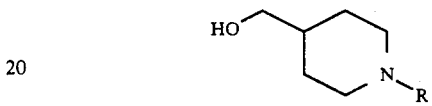

| Ex. No. | R | Notes |
|---|---|---|
| 44 | $C_6H_5CH_2$ | (a) |
| 45 | $4-(C_6H_5)C_6H_4CH_2$ | (b) |
| 46 | $1-(C_{10}H_7)CH_2$ | (c) |
| 47 | $2-(C_{10}H_7)CH_2$ | (d) |
| 48 | $C_6H_5(CH_2)_2$ | (e) |
| 49 | $C_6H_5(CH_2)_3$ | (f) |
| 50 | $2-(C_4H_3N_2)CH_2$ | (g) |
| 51 | $4-(C_4H_3N_2)CH_2$ | (h), (i) |
| 52 | $3-(C_5H_4N)CH_2$ | |
| 53 | $4-(C_5H_4N)CH_2$ | |
| 54 | $2-(C_5H_4N)CH_2$ | |
| 55 | $6-(C_9H_7N)CH_2$ | (i) |
| 56 | $4-(F-C_6H_4)CH_2$ | |
| 57 | $4-CH_3OC_6H_4CH_2$ | |
| 58 | $4-PhCH_2OC_6H_4CH_2$ | |
| 59 | $3-PhCH_2OC_6H_4CH_2$ | |
| 60 | $4-((CH_3)_2(t-Bu)-SiO)C_6H_4CH_2$ | |
| 61 | $4-CF_3C_6H_4CH_2$ | |
| 62 | $4-(N(CH_3)_2)C_6H_4CH_2$ | |
| 63 | $4-(CH_3)C_6H_4CH_2$ | |
| 64 | $4-(SCH_3)C_6H_4CH_2$ | |
| 65 | $3,4-F_2C_6H_3CH_2$ | |
| 66 | $3,4-(OCH_3)_2C_6H_3CH_2$ | |
| 67 | $3-Br-4-(OCH_3)C_6H_3CH_2$ | |
| 67A | $\underline{n}-C_6H_{13}$ | |
| 67B | cyclohexyl-$CH_2$ | |

Notes:
(a) $^1$H-NMR: 7.36-7.22(m, 5H), 3.50(s, 2H), 3.49(dd, 2H, J=7, 7), 2.94-2.86(m, 2H), 2.02-1.17(m, 8H); Anal.: Calcd. for $C_{13}H_{19}NO$: C, 76.06, H, 9.33, N, 6.82; Found: C, 75.87, H, 9.16, N, 6.55.
(b) $^1$H-NMR: 7.62-7.25(m, 9H), 3.54(s, 2H), 3.50(d, 2H, J=6), 2.98-2.92(m, 2H), 2.05-1.93(m, 2H), 1.74-1.26(m, 2H); HR-MS: Calcd.: 281.1780; Found: 281.1777. Anal. Calcd.: C, 81.10; H, 8.24; N, 4.98; Found: C, 81.19; H, 8.55; N, 5.78.
(c) $^1$H-NMR: 8.32-8.27(m, 1H), 7.86-7.71(m, 2H), 7.55-7.35(m, 4H), 3.88(s, 2H), 3.47(d, 2H, J=6), 3.00-2.92(m, 2H), 2.11-1.98(m, 2H), 1.72-1.15(m, 6H); HR-MS: Calcd.: 255.1623; Found: 255.1619; Anal. Calcd.: C, 79.96; H, 8.29; N, 5.49; Found: C, 80.37; H, 8.88; N, 4.79.
(d) m.p. 80-82° C.; Anal. Calcd.: C, 79.96; H. 8.29; N, 5.49; Found: C, 80.05; H, 8.17; N, 5.84.
(e) m.p. 88-91° C.; Anal. Calcd.: C, 76.67; H, 9.65; N, 6.39; Found: C, 76.43; H, 7.51; N, 6.26.
(f) m.p. 57-58.5° C.; $^1$H-NMR: 7.31-7.17(m, 5H), 3.48(d, 2H, J=6), 2.94(d, 2H, J=12), 2.62(t, 2H, J=8), 2.36(t, 2H, J=8), 1.97-1.23(m, 10H); HR-MS: Calcd.: 233.1780; Found: 233.1777.
(g) b.p.(°C., (Torr))154-155(0.9); Anal. Calcd.: C, 69.87; H, 8.80; N, 13.58; Found: C, 69.98; H, 8.97; N, 13.77.
(h) b.p.(°C., (Torr))166-167(0.9); Anal. Calcd.: C, 69.87; H, 8.80; N, 13.58; Found: C, 69.98; H, 9.10; N, 13.80.
(i) $C_4H_3N_2$ = pyrimidyl; $C_9H_7N$ = quinolinyl.

EXAMPLE 68

1-Benzyl-4-(4'-Fluorophenoxymethyl)piperidine

A mixture of 4 fluorophenol (6.01 g, 54 mmol), triphenylphosphine (6.87 g, 64 mmol), and 1-benzyl-4-hydroxymethylpiperidine (11.0 g, 54 mmol) in benzene (300 mL) was stirred at 10°-15° C. Diethyl azodicarboxylate (11.2 g, 10.1 mL, 64 mmol) was added dropwise. The reaction mixture was heated to reflux temperature and stirred for 24 h. The reaction mixture was cooled to ambient temperature and concentrated in vacuo. The residue was dissolved in ethyl acetate; the organic solution was washed with water three times, a 2N sodium hydroxide solution three times, dried over magnesium sulfate and filtered. Solvent was removed in vacuo to give crude product. Column chromatography (ethyl acetate:hexanes::1:1) gave, after removal of solvent, a pale yellow oil (3.88 g, 24% yield): 7.40–7.25 (m, 5H), 7.0–6.7 (m, 4H), 3.75 (d, 2H, J=4), 3.50 (s, 2H), 2.9 (br d, 2H, J=4), 2.1–1.25 (m, 7H); IR (neat): 3084(m), 3062(m), 2921(s), 2802(s), 2758(s), 1601(m), 1505(s), 1467(s), 1454(s), 1394(s); HR-MS: Calcd. for $C_{19}H_{22}FNO$: 299.1684; Found: 299.1685.

EXAMPLES 69 TO 90

Examples 69 to 90 were or could be prepared according to the procedure described for Example 68. Tetrahydrofuran can sometimes be substituted for benzene for solubility reasons.

TABLE 4

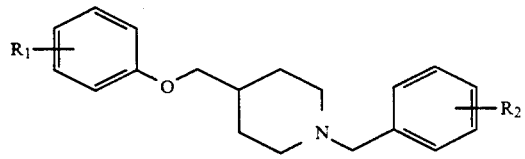

| Ex. No. | R₁ | R₂ | Notes |
| --- | --- | --- | --- |
| 68 | 4-F | H | (a) |
| 69 | 4-(CH₃) | H | (b) |
| 70 | 4-NO₂ | H | (c) |
| 71 | 4-Cl | H | (d) |
| 72 | 4-OTBDMS | H | (f) |
| 73 | 3-CH₃O | H | |
| 74 | 2-CH₃O | H | |
| 75 | 3-OTBDMS | H | (f) |
| 76 | 2-OTBDMS | H | (f) |
| 77 | 4-AcNH | H | |
| 78 | 3-NO₂ | H | |
| 79 | 3-AcNH | H | |
| 80 | 4-CF₃ | H | |
| 81 | 4-F | 4-OCH₃ | (e) |
| 82 | 4-F | 4-OAc | |
| 83 | 4-F | 4-OSi(CH₃)₂-t-Bu | |
| 84 | 4-F | 4-F | |
| 85 | 4-F | 4-NO₂ | |
| 86 | 4-F | 4-NHAc | |
| 87 | 4-F | 4-CF₃ | |
| 88 | 4-F | 4-SCH₃ | |
| 89 | 4-F | 4-SO₂CH₃ | |

TABLE 4-continued

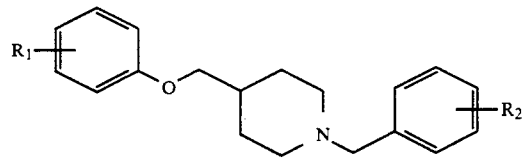

| Ex. No. | R₁ | R₂ | Notes |
| --- | --- | --- | --- |
| 90 | 4-F | 4-SO₂Et | |

Notes:
(a) 7.40–7.25(m, 5H), 7.0–6.7(m, 4H), 3.75(d, 2H, J=4), 3.50(s, 2H), 2.9(br d, 2H, J=4), 2.1–1.25(m, 7H); IR(neat): 3084(m), 3062(m), 2921(s), 2802(s), 2758(s), 1601(m), 1505(s), 1467(s), 1454(s), 1394(s); HR-MS: Calcd. for $C_{19}H_{22}FNO$: 299.1684; Found: 299.1685.
(b) m.p. 65–66° C.; Anal. Calcd.: C, 77.13; H, 8.09; N, 4.50; Found: C, 77.51; H, 8.09; N, 4.33.
(c) ¹H-NMR: 8.2(d, 2H, J=8), 7.4–7.2(m, 5H), 6.9(d, 2H, J=8), 3.9(d, 2H, J=6), 3.55(s, 2H), 3.1–2.9(m, 2H), 2.2–1.2(m, 7H). MS: 326,188. Oil.
(d) ¹H-NMR: 7.5–7.2(m, 7H), 6.8(d, 2H, J=7), 3.8(d, 2H, J=6), 3.55(s, 2H), 3.1–2.85(m, 2H), 2.15–1.2(m, 7H); MS: 315,188.
(e) ¹H-NMR: 7.2(d, 2H, J=8), 6.9(m, 6H), 3.9(s, 3H), 3.8(d, 2H, J=10), 3.5(s, 2H), 2.9(m, 2H), 2.1–1.2(m, 9H); MS: 329.
(f) TBDMS = t-butyldimethylsilyl.

EXAMPLE 91

1-(4-'-Fluorobenzyl)-4-(4'''-fluorobenzyloxymethyl)-piperidine

A solution of 4-(4'-fluorobenzyloxymethyl)piperidine (0.52 g, 2.5 mmol), 4-fluorobenzylchloride (0.036 g, 2.5 mmol) and triethylamine (0.76 g, 1.05 mL, 7.5 mmol) in tetrahydrofuran (30 mL) was stirred at reflux temperature for 24 h. The reaction mixture was cooled to room temperature and poured into a 2N sodium hydroxide solution. Three extractions with ethyl acetate, drying over magnesium sulfate, filtration and removal of solvent in vacuo gave an oil column chromatography (ethylacetate: hexanes::1:1) gave a solid (300 mg, 38% yield): m.p. 50°–53° C.; ¹H-NMR: 7.4–7.2 (m, 2H), 7.0–6.8 (m, 6H), 3.7 (d, 2H, J=7), 3.5 (s, 2H), 2.9 (d, 2H, J=7), 2.0–1.8 (m, 5H), 1.5–1.3 (m, 2H); Anal.: Calcd. for $C_{19}H_{21}F_2NO$: C,71.90, H,6.67, N,4.41; Found: C,72.31, H,6.84, N,4.29.

EXAMPLES 92 TO 113D

Examples 92 to 113D, in Tables 5 and 5A, were or could be prepared according to the procedure described for Example 91, using the appropriate benzyloxymethylpiperidine and aralkyl halide or alkyl halide.

TABLE 5

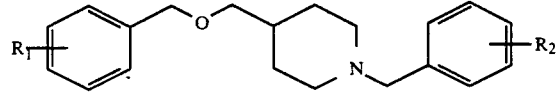

| Ex. No. | R₁ | R₂ | Notes |
| --- | --- | --- | --- |
| 91 | 4-F | 4-F | 50–53 |
| 92 | 4-F | 4-Cl | (a) |
| 93 | 4-F | 4-CH₃O | |
| 94 | 4-F | 4-NO₂ | |
| 95 | 4-F | 4-OSi(t-Bu)(CH₃)₂ | |
| 96 | 4-F | 3-OSi(t-Bu)(CH₃)₂ | |
| 97 | 4-F | 3-OCH₃ | |
| 98 | 4-F | 2,3,4,5,6-F₅ | |
| 99 | 4-F | 3,4-(OCH₃)₂ | |
| 100 | 4-F | 3,4-Cl₂ | |
| 101 | 4-F | 4-CO₂CH₃ | |
| 102 | 4-F | 3-CO₂CH₃ | |
| 103 | 4-OCH₃ | 4-CO₂CH₃ | |
| 104 | 4-OSi(Me)₂(t-Bu) | 4-CO₂CH₃ | |
| 105 | 4-NO₂ | 4-OCH₃ | |

TABLE 5-continued

[Structure: R₁-substituted benzyl-O-CH₂-piperidine-N-CH₂-benzyl-R₂]

| Ex. No. | R₁ | R₂ | Notes |
|---------|------|---------|-------|
| 106 | 4-CF₃ | 4-OCH₃ | |
| 107 | 4-CF₃ | 4-NO₂ | |
| 108 | 4-CF₃ | 4-NHAc | |
| 109 | 4-NHAc | 4-F | |
| 110 | 4-NHAc | 4-Cl | |
| 111 | 4-NHAc | 4-NO₂ | |
| 112 | 4-NHAc | 4-COCH₃ | |
| 113 | 4-NHAc | 4-CO₂CH₃ | |
| 113A | 4-Cl | 4-Cl | |

Notes:
(a) ¹H-NMR: 7.4–7.2(m, 2H), 7.0–6.8(m, 6H), 3.7(d, 2H, J=7), 3.5(s, 2H), 2.9(d, 2H, J=7), 2.0–1.8(m, 5H), 1.5–1.3(m, 2H); MS: 333.

TABLE 5A

[Structure: R₁-benzyl-O-CH₂-piperidine-N-R₄ₐ]

| Ex. No. | R₁ | R₄ₐ |
|---------|------|-----|
| 113B | 4-F | n-C₆H₁₃ |
| 113C | 4-F | cyclohexyl-CH₂ |
| 113D | 4-Cl | cyclopentyl-CH₂ |

EXAMPLES 114 TO 125

Examples 114 to 125 were or could be prepared according to the procedure described for Example 91 using the appropriate aralkyl halide and 4-benzyloxymethyl piperidine.

TABLE 6

[Structure: ArCH₂-O-CH₂-piperidine-N-CH₂-Ar']

| Ex. No. | Ar | Ar' | Notes |
|---------|---------|---------|-------|
| 114 | 4-FC₆H₄ | 2-C₁₀H₇ | (a) |
| 115 | 4-FC₆H₄ | 4-C₅H₄N | (b) |
| 116 | 4-FC₆H₄ | 2-C₉H₆N | (c) |
| 117 | 4-FC₆H₄ | 4-C₉H₆N | |
| 118 | 4-FC₆H₄ | 3-C₅H₄N | |
| 119 | 4-FC₆H₄ | 2-C₅H₄N | |
| 120 | 4-FC₆H₄ | 2-C₄H₃N₂ | (c) |
| 121 | 4-FC₆H₄ | 4-C₄H₃N₂ | |
| 122 | 4-MeOC₆H₄ | 4-C₅H₄N | |
| 123 | 4-NO₂C₆H₄ | 4-C₅H₅N | |
| 124 | 4-CF₃C₆H₄ | 4-C₅H₄N | |
| 125 | 4-FC₆H₄ | 4-FC₆H₄ | |

Notes:
(a) m.p. 85–87° C.; Anal. Calcd.: C, 78.98; H, 67.87; N, 4.01; Found: C, 79.04; H, 6.87; N, 9.13.
(b) m.p. 30–32° C.; Anal. Calcd.: C, 70.94; H, 7.06; N, 9.20; Found: C, 71.10; H, 7.10; N, 9.13 [Contains 0.25 H₂O].
(c) C₉H₆N = quinolinyl. C₄H₃N₂ = pyrimidyl.

EXAMPLES 126 TO 131

Examples 126 to 131 were or could be prepared by the procedure described for Example 68. Tetrahydrofuran can sometimes be substituted for benzene due to solubility requirements.

TABLE 7

[Structure: Ar-O-CH₂-piperidine-N-CH₂-Ar']

| Ex. No. | Ar | Ar' | Notes |
|---------|-----------|---------|-------|
| 126 | 2-(C₁₀H₇) | C₆H₅ | (a) |
| 127 | 4F-C₆H₄ | 4-C₅H₄N | |
| 128 | 4F-C₆H₄ | 3-C₅H₄N | |
| 129 | 4F-C₆H₄ | 2-C₅H₄N | |
| 130 | 4F-C₆H₄ | 4-C₄H₃N₂ | |
| 131 | 4F-C₆H₄ | 2-C₄H₃N₂ | |

Notes:
(a) b.p. 79–82° C.; Anal. Calcd.: C, 80.08; H, 7.68; N, 4.06; Found: C, 80.21; H, 7.31; N, 4.49.

EXAMPLE 132

1-(4-'-Methoxybenzyl)-4-(4''-fluorophenoxymethyl)-piperidine

A mixture of 4-(4'-fluorophenoxy)pyridine (2.26 g, 11 mmol) and 4-methoxybenzylchloride (1.72 g, 11 mmol) in N,N-dimethylformamide was stirred at 140° C. for 24 hours. Solvent was distilled from the reaction mixture in vacuo. The residue was chromatographed using chloroform-methanol (80:20) to afford 4-(4' fluorophenoxymethyl)-1-(4''-methoxybenzyl) pyridinium chloride as an oil: ¹H-NMR (DMSO-d₆): 9.3 (d, 2H, J=7), 8.2 (d, 2H, J=7), 7.5 (d, 2H, J=7), 7.1–6.9 (m, 6H), 5.8 (s, 2H), 5.5 (s, 2H), 3.8 (s, 3H).

The above pyridinium salt was dissolved in ethanol (50 mL) and cooled to 0° C. with stirring. Sodium borohydride (31.1 g, 80 mmol) was added portion-wise. The reaction mixture was stirred at 0° C. for 30 min, poured on water (100 mL), mixed and extracted three times with ethyl acetate. The combined organic layers were dried over magnesium sulfate, filtered and concentrated in vacuo. Column chromatography (ethylacetate: hexane::1:1) gave 1-(4'-methoxybenzyl)-4-(4'-fluorophenoxymethyl)-2, 3,5,6-tetrahydropyridine (2.59 g): m.p. 79°–81° C.; ¹H-NMR: 7.3 (d, 2H, J=7), 7.0–6.8 (m, 6H), 5.7 (s, 1H), 4.4 (s, 2H), 3.7 (s, 3H), 3.5 (s, 2H), 2.6 (t, 2H, J=7), 2.2 (br s, 2H); MS: 328; Anal.: Calcd. for C₂₀H₂₂FNO₂: C,73.34, H,6.77, N,4.28; Found: C,73.35, H,7.26, N,4.18.

The above tetrahydropyridine was dissolved in ethanol (50 mL) and 5% Rh-Al₂O₃ (185 mg) was added. The reaction mixture was shaken on a Parr apparatus under a hydrogen atmosphere (5 psi) until hydrogen uptake ceased.

Filtration and removal of solvent in vacuo gave material identical with Example 81.

EXAMPLE 133

1-Benzyl-4-(4'-fluorophenoxymethyl) piperidine, hydrochloride salt

1-Benzyl-4-(1'-fluorophenoxymethyl)piperidine (493 mg) (from Example 132) was dissolved in diethyl ether (10 mL). A saturated solution of hydrogen chloride in ether (10 mL) was added with stirring. Excess solvent was decanted from the oily solid, which was triturated with fresh diethyl ether. Filtration and drying in vacuo afforded a white solid (435 mg): m.p. 209°–211° C.; 'H-NMR (DMSO-d6): 7.70–7.35 (m, 5H), 7.2–6.8(m, 4H), 4.25 (d, 2H, J=3), 3.75 (d, 2H, J=3), 3.45–3.35 (m, 4H), 3.1–2.75 (m, 1H), 2.1–1.5 (m, 5H); Anal.: Calcd. for $C_{19}H_{22}FNO \cdot HCl \cdot 0.1$ $H_2O$: C,67.59, H,6.92, N,4.4; Found: C,67.32, 67.43, H,6.68, 7.03, N,4.11, 4.11.

EXAMPLES 134 TO 138

Examples 134 to 138 were or could be prepared according to the method described for Example 133 using the appropriate acid as indicated below.

TABLE 8

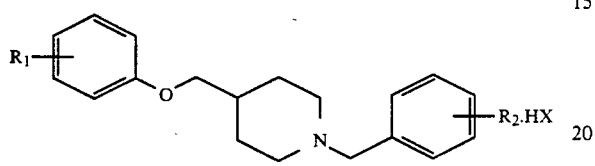

| Ex. No. | $R_1$ | $R_2$ | HX | Notes |
|---|---|---|---|---|
| 132 | 4-F | 4-OCH3 | | |
| 133 | 4-F | 4-OCH3 | HCl | 209–211 |
| 134 | 4-Cl | H | HCl | 210–212(a) |
| 135 | 4-NO2 | H | HCl | >250(b) |
| 136 | 4-CF3 | H | HCl | 225–228(c) |
| 137 | 4-F | 4-OCH3 | Maleate | 80–85(d) |
| 138 | 4-F | 4-Cl | HCl | 155–160(e) |

Notes:
(a) m.p. 210–212° C.; Anal. Calcd.: C, 64.78; H, 6.58; N, 3.98; Found: C, 64.69; H, 6.53; N, 4.06.
(b) m.p. >250° C.; Anal. Calcd.: C, 62.90; H, 6.39; N, 7.72; Found: C, 62.73; H, 6.43; N, 7.66.
(c) m.p. 225–228° C.; Anal. Calcd.: C, 62.34; H, 5.97; N, 3.64; Found: C, 62.20; H, 5.94; N, 3.70.
(d) m.p. 80–85° C.; Anal. Calcd.: C, 63.45; H, 6.39; N, 3.08; Found: C, 63.81; H, 6.21; N, 3.27. [Contains 0.5 $H_2O$].
(e) m.p. 155–160° C.; Anal. Calcd.: C, 61.79; H, 6.23; N, 3.79; Found: C, 61.94; H, 6.33; N, 3.95.

EXAMPLE 139

1-Benzyl 4-(4'-fluorobenzyloxymethyl)piperidine

A suspension of sodium hydride (60% dispersion in oil, 0.76 g, 19 mmol) in anhydrous tetrahydrofuran (38 mL) was stirred at room temperature under a nitrogen atmosphere. A solution of 1-benzyl-4-hydroxymethyl piperidine (3.82 g, 18.6 mmol) was added dropwise. After the addition was completed, the reaction mixture was stirred for 2 h. 4-Fluorobenzyl bromide (2.4 mL, 19 mmol) was added dropwise, then the reaction mixture was stirred for 72 h. Water (50 mL) was added and the resulting mixture was extracted three times with ethyl acetate. Drying over magnesium sulfate, filtration and concentration in vacuo gave an oil. Vacuum distillation (170° C. (Kugelrohr oven), 1.0 Torr) gave a colorless oil (3.45 g, 59% yield): 'H-NMR: 7.34–6.98 (m, 9H), 4.46 (s, 2H), 3.50 (s, 2H), 2.93–2.87 (m, 2H), 2.02–1.59 (m, 5H), 1.39–125 HR-MS Calcd.: 313.1478; Found: 313.1479; (m, 2H); Anal. Calcd.: for $C_{20}H_{24}FNO$: C,76.65, H,7.72, N,4.47; Found: C,77.27, H,7.69, N,4.45.

EXAMPLES 140 TO 180

Examples 140 to 180 shown in Tables 9–11, were or could be prepared using the procedure outlined in Example 139 employing the appropriate aralkyl halides or alkyl halides and 1-aralkyl-4-hydroxymethyl piperidines.

TABLE 9

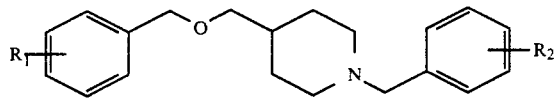

| Ex. No. | $R_1$ | $R_2$ | Notes |
|---|---|---|---|
| 139 | 4-CH3O | 4-F | |
| 140 | 4-CH3O | H | (a) |
| 141 | 4-C6H5 | H | (b) |
| 142 | 4-t-C4H9 | H | (c) |
| 143 | 4-F | 4-C6H5 | (d) |
| 144 | H | H | (e) |
| 145 | 4-CO2CH3 | H | (f) |
| 146 | 4-F | H | |
| 147 | 4-NO2 | H | |
| 148 | 4-CF3 | H | |
| 149 | 4-Cl | H | |
| 150 | 4-CH3 | H | |
| 152 | 4-CN | H | |
| 153 | 4-F | 4-CH3 | |
| 154 | 4-F | 4-NO2 | |
| 155 | 4-F | 4-CF3 | |
| 156 | 4-F | 4-OCH3 | |
| 157 | 4-F | 4-OSi(t-Bu)Me2 | |
| 158 | 4-F | 4-NHAc | |
| 159 | 4-F | 4-NO2 | |
| 160 | 4-F | 3,4-(OCH3)2 | |
| 161 | 4-F | 3,4-Cl2 | |
| 162 | 4-OCH3 | 4-F | |
| 163 | 4-OSi(t-Bu)Me2 | 4-F | |
| 164 | 4-OSi(t-Bu)Me2 | H | |
| 165 | 4-NHAc | 4-F | |
| 165A | 4-F | 4-Cl | |
| 165B | 4-Cl | 4-Cl | |

Notes:
(a) 'H-NMR: 7.32–7.22 (m, 7H), 6.87 (d, 2H, J=7), 4.42 (s, 2H), 3.80 (s, 3H), 3.48 (s, 2H), 3.28 (d, 2H, J=6), 2.88 (br d, 2H, J=11), 2.00–1.22 (m, 7H); HR-MS: Calcd.: 325.2041; Found: 325.2046.
(b) 'H-NMR: 7.61–7.23 (m, 14H), 4.53 (s, 2H), 3.48 (s, 2H), 3.35 (d, 2H, J=6), 2.29–2.86 (m, 2H), 2.01–1.26 (m, 7H); HR-MS: Calcd.: 371.2249; Found: 371.2245.
(c) 'H-NMR: 7.38–7.23 (m, 9H), 4.46 (s, 2H), 3.48 (s, 2H), 3.31 (d, 2H, J=6), 2.91–2.86 (m, 2H), 2.02–1.26 (m, 7H), 1.31 (s, 9H); MS: 351.
(d) 'H-NMR: 7.64–6.96 (m, 13H), 4.45 (s, 2H), 3.53 (s, 2H), 3.32 (d, 2H, J=6), 2.96–2.89 (m, 2H), 2.05–1.21 (m, 7H); HR-MS: Calcd.: 389.2155; Found: 389.2158.
(e) 'H-NMR: 7.34–7.21 (m, 10H), 4.50 (s, 2H), 3.48 (s, 2H), 3.32 (d, 2H, J=7), 2.91–2.84 (m, 2H), 2.00–1.24 (m, 7H); HR-MS: Calcd.: 295.1936; Found: 295.1936.
(f) 'H-NMR: 8.05–7.99 (m, 2H), 7.42–7.22 (m, 7H), 4.52 (s, 2H), 4.19 (d, 2H, J=6), 3.52 (s, 2H), 3.41 (s, 3H), 2.96–2.90 (m, 2H), 2.06–1.34 (m, 7H); HR-MS: Calcd.: 353.1991; Found: 353.1987.

TABLE 9A

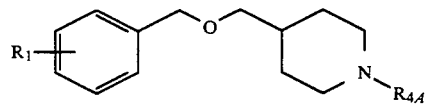

| Ex. No. | $R_1$ | $R_{4A}$ |
|---|---|---|
| 165C | 4-Cl | n-C5H11 |
| 165D | 4-F | n-C6H13 |

TABLE 10

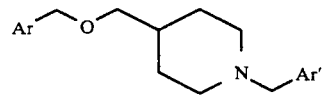

| Ex. No. | Ar | Ar' | Notes |
|---|---|---|---|
| 166 | 3,5-dimethylisoxazol-2-methyl | C6H5 | (a) |
| 167 | 4-F—C6H4 | 4-(C5H4N) | (b) |
| 168 | 3-(C5H4N) | C6H5 | (c) |
| 169 | 2-quinolinylmethyl | C6H5 | (d) |
| 170 | 4-F—C6H4 | 2-(C5H4N) | (e) |

TABLE 10-continued

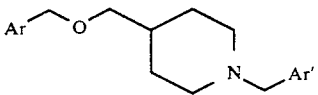

| Ex. No. | Ar | Ar' | Notes |
|---|---|---|---|
| 171 | 4-F—C$_6$H$_4$ | 2-(C$_{10}$H$_7$) | (f) |
| 172 | 4-F—C$_6$H$_4$ | 1-(C$_{10}$H$_7$) | (g) |
| 173 | 4-F—C$_6$H$_4$ | 4-(C$_6$H$_5$)C$_6$H$_4$ | (h) |

Notes:
(a) $^1$H-NMR: 7.32–7.21 (m, 5H), 4.43 (s, 2H), 3.48 (s, 2H), 3.24 (d, 2H, J=6), 2.88 (br d, 2H, J=12), 2.35 (s, 3H), 2.24 (s, 3H), 2.16–1.22 (m, 7H); MS: 315.
(b) $^1$H-NMR: 8.53 (d, 2H, J=6), 7.33–7.24 (m, 4H), 7.02 (t, 2H, J=9), 4.45 (s, 2H), 3.47 (s, 2H), 3.31 (d, 2H, J=6), 2.84 (br d, 2H, J=11), 2.05–1.26 (m, 7H); HR-MS: Calcd.: 314.1794; Found: 314.1794.
(c) $^1$H-NMR: 8.56–8.52 (m, 2H), 7.69–7.64 (m, 1H), 7.32–7.20 (m, 6H), 4.50 (s, 2H), 3.49 (s, 2H), 3.34 (d, 2H, J=6), 2.83 (br d, 2H, J=12), 2.04–1.20 (m, 7H); HR-MS: Calcd.: 296.1888; Found: 296.1886.
(d) m.p. 75–77° C.; $^1$H-NMR: 8.19–7.22 (m, 11H), 4.79 (s, 2H), 3.50 (s, 2H), 3.43 (d, 2H, J=6), 2.94–2.88 (m, 2H), 2.03–1.24 (m, 7H); MS: 346.
(e) $^1$H-NMR: 8.55 (d, 1H, J=4), 7.68–6.97 (m, 7H), 4.45 (s, 2H), 3.63 (s, 2H), 3.31 (d, 2H, J=6), 2.93–2.87 (m, 2H), 2.12–1.29 (m, 7H); HR-MS: Calcd.: 313.1716; Found: 313.1716.
(f) m.p. 77.5–78.5° C.; $^1$H-NMR: 7.83–7.73 (m, 4H), 7.51–7.40 (m, 3H), 7.33–7.24 (m, 2H), 7.07–6.96 (m, 2H), 4.45 (s, 2H), 3.64 (s, 2H), 3.31 (d, 2H, J=6), 2.96–2.90 (m, 2H), 2.66–1.21 (m, 7H); HR-MS: Calcd.: 363.1999; Found: 363.2000.
(g) $^1$H-NMR: 8.33–8.28 (m, 1H), 7.86–7.71 (m, 2H), 7.54–7.25 (m, 6H), 7.07–6.95 (m, 2H), 4.44 (s, 2H), 3.87 (s, 2H), 3.29 (d, 2H, J=6), 2.97–2.91 (m, 2H), 2.09–1.98 (m, 2H), 1.74–1.57 (m, 3H), 1.36–1.16 (m, 2H); HR-MS: Calcd. 363.1998; Found: 363.1999.
(h) $^1$H-NMR: 7.64–6.96 (m, 13H), 4.45 (s, 2H), 3.53 (s, 2H), 3.32 (d, 2H, J=6), 2.96–2.89 (m, 2H), 2.05–1.21 (m, 7H); HR-MS: Calcd.: 389.2155; Found: 389.2158.

TABLE 11

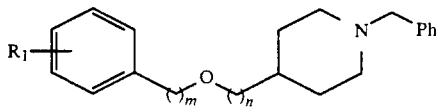

| Ex. No. | R$_1$ | m | n | Notes |
|---|---|---|---|---|
| 174 | H | 3 | 0 | (a) |
| 175 | H | 3 | 1 | (b) |
| 176 | H | 4 | 1 | (c) |
| 177 | H | 5 | 1 | (d) |
| 178 | 4-t-C$_4$H$_9$ | 1 | 2 | (e) |
| 179 | 4-F | 1 | 2 | (f) |
| 180 | 4-F | 1 | 0 | (g) |

Notes:
(a) $^1$H-NMR: 7.33–7.16 (m, 10H), 3.48 (s, 2H), 3.43 (t, 2H, J=6), 3.33–3.21 (m, 1H), 2.80–264 (m, 4H), 2.33–1.50 (m, 8H); HR-MS: Calcd.: 309.2092; Found: 309.2101.
(b) $^1$H-NMR: 7.32–7.16 (m, 10H), 3.49 (s, 2H), 3.39 (t, H, J=7), 3.25 (d, 2H, J=7), 2.90 (br d, J=11), 2.68 (t, 2H, J=8), 2.04–1.24 (m, 9H); HR-MS: Calcd.: 323.2249; Found: 323.2249.
(c) $^1$H-NMR: 7.32–7.15 (m, 10H), 3.48 (s, 2H), 3.40 (t, 2H, J=6), 3.23 (d, 2H, J=6), 2.88 (br d, 2H, J=12), 2.62 (t, 2H, J=7), 2.00–1.21 (m, 11H); HR-MS: Calcd.: 337.2406; Found: 337.2407.
(d) $^1$H-NMR: 7.34–7.12 (m, 10H), 3.49 (s, 2H), 3.38 (t, 2H, J=6), 3.23 (d, 2H, J=6), 2.91–2.86 (br d, 2H, J=12), 2.60 (t, 2H, J=7), 2.01–1.22 (m, 13H); HR-MS: Calcd.: 351.2562; Found: 351.2562.
(e) $^1$H-NMR: 7.39–7.23 (m, 9H), 4.45 (s, 2H), 3.49 (t, 2H, J=6), 3.48 (s, 2H), 2.88–2.82 (m, 2H), 1.99–1.21 (m, 9H), 1.31 (s, 9H); MS: 365.
(f) $^1$H-NMR: 7.32–7.26 (m, 7H), 7.06–6.97 (m, 4H), 4.44 (s, 2H), 3.48 (s, 2H), 3.48 (t, 2H, J=6), 2.89–2.83 (m, 2H), 1.94–1.22 (m, 9H).
(g) b.p. 153° C. (0.8 Torr); $^1$H-NMR: 7.34–7.23 (m, 7H), 7.05–6.97 (m, 2H), 4.49 (s, 2H), 3.49 (s, 2H), 3.45–3.38 (m, 1H), 2.78–2.70 (m, 2H), 2.20–1.63 (m, 6H); HR-MS: Calcd.: 299.1685; Found: 299.1679.

EXAMPLES 181 TO 205

Examples 181 to 205, shown in Tables 12 to 14, were or could be prepared according to the method outlined for Example 133, using the appropriate acid.

TABLE 12

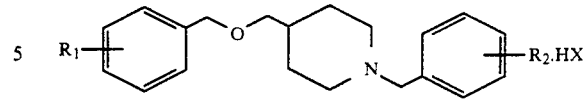

| Ex. No. | R$_1$ | R$_2$ | HX | Notes |
|---|---|---|---|---|
| 181 | 4-F | H | maleate | (a) |
| 182 | 4-CH$_3$O | H | maleate | (b) |
| 183 | 4-C$_6$H$_5$ | H | maleate | (c) |
| 184 | 4-t-C$_4$H$_9$ | H | HCl | (d) |
| 185 | H | H | HCl | (e) |
| 186 | 4-CO$_2$CH$_3$ | H | HCl | (f) |
| 187 | 4-F | 4-CO$_2$CH$_3$ | HCl | (g) |
| 188 | 4-F | 4-Cl | HCl | (h) |
| 189 | 4-F | 4-OH | HCl | (i) |
| 190 | 4-F | 4-OCH$_2$Ph | HCl | (j) |

Notes:
(a) m.p. 115–116° C.; Anal. Calcd.: C, 67.12; H, 6.57; N, 3.26; Found: C, 67.05; H, 6.41; N, 2.98.
(b) m.p. 93–95° C.; Anal. Calcd.: C, 68.01; H, 7068; N, 3.17; Found: C, 67.76; H, 6.87; N, 3.25.
(c) m.p. 113–119° C.; Anal. Calcd.: C, 72.58; H, 6.85; N, 2.82; Found: C, 72.33; H, 6.92; N, 3.06. [Contains 0.5 H$_2$O].
(d) m.p. 186–188° C.; Anal. Calcd.: C, 74.30; H, 8.83; N, 3.61; Found: C, 73.60; H, 8.62; N, 4.18.
(e) m.p. 158–160° C.; Anal. Calcd.: C, 72.38; H, 7.90; N, 4.22; Found: C, 72.21; H, 7.74; N, 4.47.
(f) m.p. 169–170° C.; Anal. Calcd.: C, 67.42; H, 7.72; N, 3.57; Found: C, 66.94; H, 7.34; N, 3.53.
(g) m.p. 188–189° C.; Anal. Calcd. for C$_{22}$H$_{27}$ClFNO$_3$: C, 64.78, H, 6.67, N, 3.43; Found: C. 64.83; H, 6.96, N, 3.33.
(h) m.p. 181–183° C.; Anal.: Calcd. for C$_{20}$H$_{24}$Cl$_2$FNO: C, 62.50, H, 6.29, N, 3.64; Found: C, 62.95, H, 6.23, N, 3.83.
(i) m.p. 134–135° C.; Anal.: Calcd. for C$_{20}$H$_{24}$FNO$_2$.HCl: C, 65.66, H, 6.89, N, 3.83; Found: C. 65.75; H, 7.02, N, 3.77.
(j) m.p. 182–184° C.; Anal.: Calcd. for C$_{27}$H$_{30}$FNO$_2$.HCl: C, 71.12, H, 6.85, N, 3.07; Found: C, 71.25, H, 6.96, N, 3.05.

TABLE 13

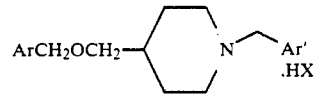

| Ex. No. | Ar | Ar$^1$ | HX | Notes |
|---|---|---|---|---|
| 191 | 3,5-dimethyl isoxazol-2-yl-methyl | C$_6$H$_5$ | maleate | (a) |
| 192 | 4-FC$_6$H$_4$ | 4-(C$_5$H$_4$N) | maleate | (b) |
| 193 | 3-(C$_5$H$_4$N) | C$_6$H$_5$ | maleate | (c) |
| 194 | 2-quinolinyl methyl | C$_6$H$_5$ | HCl | (d) |
| 195 | 4-FC$_6$H$_4$ | 2-(C$_{10}$H$_7$) | HCl | (e) |
| 196 | 4-FC$_6$H$_4$ | 1-(C$_{10}$H$_7$) | HCl | (f) |
| 197 | 4-FC$_6$H$_4$ | 4-(C$_6$H$_5$)C$_6$H$_4$ | HCl | (g) |

Notes:
(a) m.p. 131–132° C.; Anal. Calcd.: C, 64.17; H, 7.02; N, 6.51; Found: C, 64.39; H, 6.98; N, 6.63.
(b) m.p. 96–102° C.; Anal. Calcd.: C, 64.17; H, 6.32; N, 6.51; Found: C, 63.96; H, 6.14; N, 6.25.
(c) m.p. 68–73° C.; Anal. Calcd.: C, 66.97; H, 6.84; N, 6.79; Found: C, 65.18; H, 6.76; N, 6.52.
(d) m.p. 169–171° C.; Anal. Calcd.: C, 72.14; H, 7.11; N, 7.32; Found: C, 72.24; H, 7.21; N, 6.96.
(e) m.p. 172–173° C.; Anal. Calcd.: C, 72.08; H, 6.81; N, 3.50; Found: C, 71.97; H, 7.10; N, 3.75.
(f) m.p. 175–176° C.; Anal. Calcd.: C, 72.02; H, 6.81; N, 3.50; Found: C, 72.17; H, 7.11; N, 3.58.
(g) m.p. 195–196° C.

TABLE 14

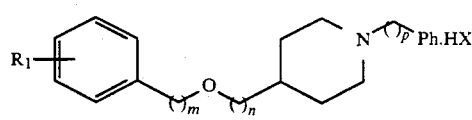

| Ex. No. | R¹ | m | n | p | HX | Notes |
|---|---|---|---|---|---|---|
| 198 | H | 3 | 0 | 1 | maleate | (a) |
| 199 | H | 3 | 1 | 1 | maleate | (b) |
| 200 | H | 4 | 1 | 1 | HCl | (c) |
| 201 | H | 5 | 1 | 1 | HCl | (d) |
| 202 | 4-F | 1 | 2 | 1 | HCl | |
| 203 | 4-F | 1 | 0 | 1 | HCl | (e) |
| 204 | 4-F | 2 | 0 | 1 | HCl | |
| 205 | 4-F | 1 | 1 | 1 | Fumarate | |

Notes:
(a) m.p. 94–96° C.; Anal. Calcd.: C, 70.57; H, 7.34; N, 3.29; Found: C, 70.68; H, 7.55; N, 3.43.
(b) m.p. 85–87° C.; Anal. Calcd.: C, 71.05; H, 7.57; N, 3.19; Found: C, 70.72; H, 7.31; N, 2.99.
(c) m.p. 125–127° C.; Anal. Calcd.: C, 73.87; H, 8.63; N, 3.75; Found: C, 73.62; H, 8.49; N, 3.84.
(d) Anal. Calcd.: C, 74.30; H, 8.83; N, 3661; Found: C, 74.13; H, 9.15; N, 3.52.
(e) m.p. 146–148° C.; Anal. Calcd.: C, 67.95; H, 6.90; N, 4.17; Found: C, 67.59; H, 6.93; N, 3.69.

EXAMPLE 206

1-Benzyl-3-(4'-fluorobenzyloxymethyl) piperidine, maleate salt

Following the procedure for Example 139, 4-fluorobenzylbromide and 1-benzyl-3-(hydroxy-methyl)-piperidine were reacted to give 1-benzyl-3-(4'-fluorobenzyloxymethyl) piperidine.

Following the procedure for Example 133, the above piperidine was converted to its maleate salt: m.p. 127°–129°; Anal.: Calcd. for $C_{24}H_{28}FNO_5$: C,67.12, H,6.57, N,3.26; Found: C,66.66, H,6.53, N,3.42.

EXAMPLE 207

1-Benzyl-2-(4'-fluorophenoxymethyl) piperidine, hydrochloride salt

Following the procedure for Example 139, 4-fluorobenzylbromide and 1-benzyl-2-(hydroxymethyl)-piperidine were reacted to give 1-benzyl-2-(4'-fluorophenoxymethyl) piperidine.

Following the procedure for Example 133, the above piperidine was converted to its hydrochloride salt: m.p. 41°–142° C.; Anal.: Calcd. for $C_2H_{25}ClFNO$: C,68.66, H,7.20, N,4.00; Found: C,68.46, H,7.45, N,4.11.

EXAMPLE 208

4-(4'-Fluorobenzyloxymethyl) piperidine

1-Benzyl-4-(4'-fluorobenzyloxy) piperidine (15.2 g, 48.6 mmol) and methyl chloroformate (4.5 mL, 58 mmol) were dissolved in benzene (150 mL) and the resulting solution was stirred at reflux temperature for 16.5 h. The reaction mixture was cooled to ambient temperature and solvent was removed on a rotary evaporator. Vacuum distillation (b.p. 163°–174° C., 0.9 Torr) gave 1-carbomethoxy-4-(4'-fluorobenzyloxymethyl) piperidine, a colorless oil (13.3 g); Anal.: Calcd. for $C_{15}H_{20}FNO_3$: C,64.04, H,7.17, N,4.98; Found: C,64.08, H,7.46, N,5.28.

The above carbamate (13.3 g, 47.3 mmol) and potassium hydroxide (35 g, 625 mmol) were dissolved in a mixture of water (30 mL) and methanol (120 mL). The mixture was stirred at reflux temperature for 20 h. The reaction mixture was concentrated in vacuo after being cooled to room temperature. The residue was dissolved in ethylacetate; the organic solution was washed with water three times, then with brine. Drying over magnesium sulfate, filtration and removal of solvent in vacuo gave an oil. Vacuum distillation (b.p 116°–127° C., 0.4 Torr) afforded 4-(4'-fluorobenzyloxymethylpiperidine), a colorless oil (10.2 g, 87% yield); Anal.: Calcd. for $C_{13}H_{18}FNO$: C,69.93, H,8.13, N,6.27; Found: C,70.11, H,7.85, N,6.25.

EXAMPLE 209 TO 290

Examples 209 to 290 were or could be prepared according to the procedure described for Example 208, using the appropriate 1-benzyl piperidine derivatives.

TABLE 15

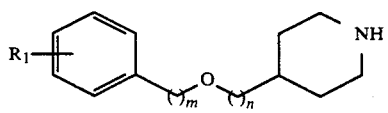

| Ex. No. | m | n | R₁ |
|---|---|---|---|
| 206 | 1 | 1 | 4-F |
| 207 | 0 | 1 | 4-F |
| 208 | 1 | 1 | 4-F |
| 209 | 0 | 1 | 3-F |
| 210 | 0 | 2 | 2-F |
| 211 | 0 | 1 | 2,3,4,5,6-F₅ |
| 212 | 0 | 1 | 4-Cl |
| 213 | 0 | 1 | 3-Cl |
| 214 | 0 | 1 | 2-Cl |
| 215 | 0 | 1 | 4-NO₂ |
| 216 | 0 | 1 | 3-NO₃ |
| 217 | 0 | 1 | 2-NO₂ |
| 218 | 0 | 1 | 4-CF₃ |
| 219 | 0 | 1 | 3-CF₃ |
| 220 | 0 | 1 | 2-CF₃ |
| 221 | 0 | 1 | 4-NHCH₂Ph |
| 222 | 0 | 1 | 3-NHCH₂Ph |
| 223 | 0 | 1 | 4-OCH₃ |
| 224 | 0 | 1 | 3-OCH₃ |
| 225 | 0 | 1 | 2-OCH₃ |
| 226 | 0 | 1 | 3,4-Cl₂ |
| 227 | 0 | 1 | 4-SCH₃ |
| 228 | 0 | 1 | 3-SCH₃ |
| 229 | 0 | 1 | 4-SO₂CH₃ |
| 230 | 0 | 1 | 3-SO₂CH₃ |
| 231 | 0 | 1 | 2-SO₂CH₃ |
| 232 | 0 | 1 | 4-Br |
| 233 | 0 | 1 | 3-Br |
| 234 | 0 | 1 | 2-Br |
| 235 | 0 | 1 | 3,4-F₂ |
| 236 | 0 | 1 | 4-S(O)CH₃ |
| 237 | 0 | 1 | 3-S(O)CH₃ |
| 238 | 0 | 1 | 4-OSi(t-Bu)(CH₃)₂ |
| 239 | 0 | 1 | 3-OSi(t-Bu)(CH₃)₂ |
| 240 | 0 | 1 | 3,4-(OCH₃)₂ |
| 241 | 0 | 1 | 4-CH₃ |
| 242 | 0 | 1 | 3-CH₃ |
| 243 | 0 | 1 | 4-Br, 3-OCH₃ |
| 244 | 0 | 1 | 4-OCH₃, 3-Br |
| 245 | 0 | 1 | 4-F, 3-NO₂ |
| 246 | 0 | 1 | 4-ET |
| 247 | 0 | 1 | 3-ET |
| 248 | 0 | 1 | 4-Pr |
| 249 | 0 | 1 | 3-Pr |
| 250 | 1 | 1 | 3-F |
| 251 | 1 | 1 | 2-F |
| 252 | 1 | 1 | 4-F |
| 253 | 1 | 1 | 2,3,4,5,6-F₅ |
| 254 | 1 | 1 | 4-Cl |
| 255 | 1 | 1 | 3-Cl |
| 256 | 1 | 1 | 2-Cl |
| 257 | 1 | 1 | 4-NO₂ |
| 258 | 1 | 1 | 3-NO₂ |
| 259 | 1 | 1 | 2-NO₂ |
| 260 | 1 | 1 | 4-CF₃ |
| 261 | 1 | 1 | 3-CF₃ |

TABLE 15-continued

R₁ substituted benzyl-O-(CH₂)ₘ-(CH₂)ₙ-piperidine-NH structure

| Ex. No. | m | n | R₁ |
|---|---|---|---|
| 262 | 1 | 1 | 2-CF₃ |
| 263 | 1 | 1 | 4-PhO |
| 265 | 1 | 1 | 4-OCH₃ |
| 266 | 1 | 1 | 3-OCH₃ |
| 267 | 1 | 1 | 2-OCH₃ |
| 268 | 1 | 1 | 3,4-Cl₂ |
| 269 | 1 | 1 | 4-SCH₃ |
| 270 | 1 | 1 | 3-SCH₃ |
| 271 | 1 | 1 | 4-SO₂CH₃ |
| 272 | 1 | 1 | 3-SO₂CH₃ |
| 273 | 1 | 1 | 2-SO₂CH₃ |
| 274 | 1 | 1 | 4-Br |
| 275 | 1 | 1 | 3-Br |
| 276 | 1 | 1 | 3,4-F₂ |
| 277 | 1 | 1 | 4-S(O)CH₃ |
| 278 | 1 | 1 | 3-S(O)CH₃ |
| 279 | 1 | 1 | 4-Ph |
| 280 | 1 | 1 | 3-Ph |
| 281 | 1 | 1 | 3,4-(OCH₃)₂ |
| 282 | 1 | 1 | 4-CH₃ |
| 283 | 1 | 1 | 3-CH₃ |
| 284 | 1 | 1 | 4-Br, 3-OCH₃ |
| 285 | 1 | 1 | 4-OCH₃, 3-Br |
| 286 | 1 | 1 | 4-F, 3-NO₂ |
| 287 | 1 | 1 | 4-PhCO |
| 288 | 1 | 1 | 3-PhCO |
| 289 | 1 | 1 | 4-PhCH₂O |
| 290 | 1 | 1 | 3-PhCH₂O |

EXAMPLE 291

1-Benzyl-4-(2'-6''-fluorobenzthiazolyl)oxymethylpiperidine hyrochloride salt

Sodium hydride (60% dispersion in oil, 0.33 g, 8.2 mmol) was suspended in anhydrous tetrahydrofuran (10 mL) under a nitrogen atmosphere with stirring. A solution of 1-benzyl-4-hydroxymethylpiperidine (1.40 g, 6.83 mmol) in anhydrous tetrahydrofuran (10 mL) was added dropwise. 2-Chloro-6-fluorobenzothiazole (1.28 g, 6.84 mmol) was added in one portion and the reaction mixture was heated to reflux temperature for 24 h. The mixture was cooled to ambient temperature and water (20 mL) was added slowly. Three extractions with ethyl acetate, drying the combined organic layers over magnesium sulfate, filtration and removal of solvent in vacuo gave the product as a yellow solid (1.81 g, 74% yield).

The product was dissolved in diethyl ether and treated with a 1M solution of hydrogen chloride in ether (5.7 mL, 5.7 mmol). The precipitate was filtered and washed with copious amounts of diethyl ether.

Drying in vacuo gave 1-benzyl-4-(2'-(6''-fluorobenzothiazolyl)oxymethyl piperidine, hydrochloride salt, a white solid (1.75 g, 95% yield): m.p. 201°–203° C.; Anal.: Calcd. for C₂₀H₂₁FNO₂S.HCl: C,61.14, H,5.64, N,7.13; Found: C,61.15, H,5.72, N,6.93.

EXAMPLES 292 TO 308

Examples 292 to 308 were or could be prepared according to the method described for Example 291 using the appropriate heteroarylhalide and/or making the appropriate acid addition salt. N,N-Dimethylformamide, N,N-dimethylacetamide or N-methylpyrrolidone can be used for cases requiring higher temperatures.

TABLE 16

ArO(CH₂)ₘ-piperidine-N-CH₂-Ar'.HX

| Ex. No. | m | Ar | Ar¹ | HX | Notes |
|---|---|---|---|---|---|
| 291 | 1 | 6-fluorobenzo-thiazol-2-yl | Ph | HCl | 201–203ᵃ |
| 292 | 0 | 6-fluorobenzo thiazol-2-yl | Ph | HCl | (b) |
| 293 | 0 | benzothiazol-2-yl | Ph | HCl | (c) |
| 294 | 1 | benzothiazol-2-yl | Ph | HCl | (d) |
| 295 | 0 | 2-pyrimidyl | Ph | | |
| 296 | 1 | 2-pyrimidyl | Ph | | |
| 297 | 0 | 2-pyrimidyl | Ph | | |
| 298 | 1 | 2-pyridyl | Ph | | |
| 299 | 0 | 2-thiazolyl | Ph | | |
| 300 | 1 | 2-thiazolyl | Ph | | |
| 301 | 0 | 2-imidazolyl | Ph | | |
| 302 | 1 | 2-imidazolyl | Ph | | |
| 303 | 0 | 2-oxazolyl | Ph | | |
| 304 | 1 | 2-oxazolyl | Ph | | |
| 305 | 0 | 2-benzimidazolyl | Ph | | |
| 306 | 1 | 2-benzimidazolyl | Ph | | |
| 307 | 0 | 2-quinolinyl | Ph | | |
| 308 | 1 | 2-quinolinyl | Ph | | |

Notes:
(a) m.p. 201–203° C.
(b) m.p. 51–53° C. Anal.: Calcd. for C₉H₁₀FN₂OS.HCl: C, 60.23, H, 5.32, N, 7.39; Found: C, 59.97, H, 5.35, N, 7.32
(c) m.p. 203–204° C. Anal.: Calcd. for C₁₉H₂₀FN₂OS.HCl: C, 63.23, H, 5.87, N, 7.76; Found: C, 63.31, H, 6.01, N, 7.54
(d) m.p. 193–198° C. Anal.: Calcd. for C₂₀H₂₂N₂OS.HCl: C, 64.07, H, 6.18, N, 7.47; Found: C, 64.15, H, 6.01, N, 7.26.

EXAMPLE 309

1-(2'-Pyridylmethyl)-4-(4''-fluorobenzyloxymethyl)piperidine, hydrochloride salt Following the procedure of Example 133, 1-(2'-pyridylmethyl)-4-(4''-fluorobenzyloxymethyl)piperidine was treated with anhydrous hydrogen chloride in ether to give the title compound, a gummy solid: HR-MS: Calcd: 13.1716; Found: 313.1716.

EXAMPLE 310

1-Benzyl-4-(2'-naphthyloxymethyl)piperidine

Part A: 1-Benzoyl-4-hydroxymethylpiperidine

A solution of lithium borohydride in tetrahydrofuran (2 M, 0.95 mL, 1.9 mmol) was added dropwise to a solution of ethyl 1-benzoylpiperidine-4-carboxylate (1 g, 3.8 mmol) in tetrahydrofuran (10 mL) with stirring under a nitrogen atmosphere. The reaction mixture was stirred for 18 h, poured onto water and extracted three times with ethyl acetate. The combined organic layers were dried over magnesium sulfate, filtered and concentrated in vacuo. Column chromatography (ethylacetate) afforded 1-benzoyl-4-hydroxymethylpiperidine, a solid (522 mg, R/=0.14): m.p. 85°–87° C.; ¹H-NMR (CDCl₃, 200 MHz): 7.45–7.35 (m, 5H), 4.8–4.6 (m, 1H), 3.9–3.7 (m, 1H), 3.5 (br s, 2H), 3.2–3.6 (m, 3H), 2.25 (br s, 1H), 2.0–1.6 (m, 3H), 1.4–1.0 (m, 2H); HRMS: Calcd. for C₁₃H₁₇NO₂:219.1259; Found: 19.1245.

Part B: 1-Benzoyl-4-(2'-naphthyloxymethyl)piperidine

A mixture of the product from Part A, thionyl chloride (5 mL) and chloroform (40 mL) was stirred at reflux temperature for 1 hr. Solvent was then removed in vacuo to afford crude 1-benzoyl-4-chloromethyl-piperidine.

A solution of 2-naphthol (0.7 g, 4.8 mmol) in tetrahydrofuran was added dropwise to a suspension of sodium hydride (0.23 g, 50% in oil, prewashed with hexane) in N,N-dimethylformamide (20 mL). The reaction mixture was stirred at room temperature for 30 min, then a solution of the crude chloride in N,N-dimethylformamide (5 mL) was added dropwise. The reaction mixture was stirred at reflux temperature for 24 h. Solvent was distilled in vacuo; the residue was taken up in water and extracted three times with ethyl acetate. The combined organic layers were dried over magnesium sulfate, filtered and concentrated in vacuo. Column chromatography (ethyl acetate:hexanes::3:7) afforded 1-benzoyl-4-(2'-naphthyloxymethyl)piperidine (350 mg):m.p. 110°–113° C.; 'H-NMR (CDCl$_3$, 200 MHz): 7.7 (m, 2H), 7.5–7.2 (m, 10H), 4.8 (br s, 1H), 4.0 (br d, 2H, J=8), 3.0 (m, 3H), 2.3–1.3 (m, 5H); Anal.: Calcd. for $C_{23}H_{23}NO_2 \cdot 0.5H_2O$: C,77.94, H,6.77, N,3.96; Found: C,77.94, 78.07, H,6.87, 6.93, N,4.42, 4.37.

Part C: 1-Benzyl-4-(2'-naphthyloxymethyl)piperidine

A mixture of the product from Part B, lithium aluminum hydride (1.0 M in tetrahydrofuran, 0.41 mL, 0.41 mmol) and tetrahydrofuran (20 mL) was stirred at reflux temperature for 5 h. The reaction mixture was cooled to room temperature, quenched with excess ethyl acetate and water. The layers were separated; the aqueous layer was extracted twice with ethyl acetate. The combined organic layers were dried over magnesium sulfate, filtered and concentrated in vacuo. Column chromatography (ethyl acetate:hexane::1:1) afforded the title compound, which was identical to the product of Example 126.

Examples 311 to 315 may be prepared according to the procedures described for Examples 68, 91, 139, 208, 309, 310 or any combination thereof (Table 17).

TABLE 17

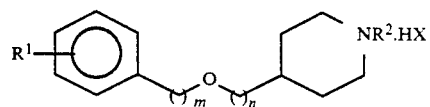

| Ex. # | R$^1$ | m | n | R$^2$ | Notes |
|---|---|---|---|---|---|
| 309 | 4-F | 1 | 1 | 2'-pyridylmethyl | |
| 311 | 4-F | 1 | 1 | cyclohexyl | (a) |
| 312 | 4-F | 1 | 1 | hexyl | (b) |
| 313 | 4-F | 1 | 1 | (CH$_2$)$_3$Ph | (c) |
| 314 | 4-F | 1 | 1 | CH$_2$CH=C(CH$_3$)$_2$ | (d) |
| 315 | 4-F | 1 | 0 | CH$_2$Ph | (e) |

Footnotes for Table 17
(a) HX=HCl; Anal.: Calcd for $C_{20}H_{30}FNO$—HCl: C, 67.49, H, 8.78, N, 3.94; Found: C, 67.37, H, 8.71, N, 4.13.
(b) HX=HCl; m.p. 158–160° C.; Anal.: Calcd for $C_{19}H_{30}FNO$—HCl: C, 66.36, H, 9.09, N, 4.07; Found: C, 66.66, H, 9.17, N, 4.17.
(c) HX=HCl; m.p. 146–149° C.; Anal.: Calcd for $C_{22}H_{28}FNO$—HCl: C, 69.92, H, 7.73, N, 3.71; Found: C, 69.90, 69.89, H, 7.97, 7.91, N, 2.02, 2.14.
(d) HX=HCl; Anal.: Calcd for $C_{18}H_{26}FNO$—HCl: C, 65.94, H, 8.30; N, 4.27; Found: C, 65.26, 65.12, H, 8.09, 7.79, N, 3.75, 3.88.
(e) HX=HCl; Anal.: Calcd for $C_{19}H_{22}FNO$—HCl: C, 67.95, H, 6.90; N, 4.17; Found: C, 67.36, 67.59, H, 6.78, 6.93, N, 3.74, 3.69.

Pharmaceutical Utility

The compounds of this invention and pharmaceutically acceptable salts thereof possess psychotropic properties, particularly antipsychotic activity of good duration with selective sigma receptor antagonist activities while lacking the typical movement disorder side-effects of standard dopamine receptor antagonist antipsychotic agents. These compounds may also be useful to treat drug induced psychosis caused by certain psychotomimetic agents, such as phencyclidine (PCP), and also are useful as antidyskinetic agents.

In Vitro

Sigma Receptor Binding Assay

Male Hartley guinea pigs (250–300 g, Charles River) were sacrificed by decapitation. Brain membranes were prepared by the method of Tam (*Proc. Natl. Acad. Sci. USA* 80: 6703–6707, 1983). Whole brains were homogenized (20 sec.) in 10 vol (wt/vol) of ice-cold 0.34M sucrose with a Brinkmann Polytron (setting 8). The homogenate was centrifuged at 920×g for 10 min. The supernatant was centrifuged at 47,000×g for 20 min. The resulting membrane pellet was resuspended in 10 vol (original wt/vol) of 50 mM Tris HCl (pH 7.4) and incubated at 37° C. for 45 min to degrade and dissociate bound endogenous ligands. The membranes were then centrifuged at 47,000 ×g for 20 min and resuspended in 50 mM Tris HCl (50 mL per brain).

0.5 mL aliquots of the membrane preparation were incubated with unlabeled drugs, 1 nM (+)-[$^3$H]SKF 10,047 in 50 mM Tris HCl, pH 7.4, in a final volume of 1 mL. Nonspecific binding was measured in the presence of 10 μM (+)-SKF 10,047. The apparent dissociation constant (k$_d$) for (+)-[$^3$H]SKF 10,047 is 50 nM. After 45 min of incubation at room temperature, samples were filtered rapidly through Whatman GF/C glass filters under negative pressure, and washed 3 times with ice-cold Tris buffer (5 mL).

IC$_{50}$s were calculated from log-logit plots. Apparent k$_i$s were calculated from the equation, $K_i = IC_{50}/[1+(L/K_d)]$ (4), where L is the concentration of radioligand and K$_d$ is its dissociation constant. Data are shown in Table I.

Dopamine Receptor Binding

Membranes were prepared from guinea pig striatum by the method described for sigma receptor binding. The membranes were then resuspended in 50 mM Tris HCl (9 mL per brain).

0.5 mL aliquots of the membrane preparation were incubated with unlabeled drugs, and 0.15 nM [$^3$H]spiperone in a final volume of 1 mL containing 50 mM Tris HCl, 120 mM NaCl and 1 mM MgCl$_2$ (pH 7.7). Nonspecific binding was measured in the presence of 100 nM (+)-butaclamol. After 15 min of incubation at 37° C., samples were filtered rapidly through Whatman GF/C glass filters under negative pressure, and washed three times with ice-cold binding buffer (5 mL). Data are shown in Table I.

The data in Table I indicate that haloperidol, a typical antipsychotic drug, has potent binding affinity for both the sigma and dopamine receptors. This binding profile of haloperidol reflects the therapeutic activity as well as the motor side effects caused by antagonism of the dopamine receptors. In contrast, the examples of this invention shown in Table I indicate potent and selective binding affinity for sigma receptors without binding to the dopamine receptors or have weak binding for the dopamine receptor. Therefore these compounds are not expected to produce the extrapyramidal symptoms that are typical of that produced by haloperidol and other typical antipsychotics that are dopamine receptor antagonists.

In Vivo

Isolation-Induced Aggression in Mice

This is a modification of the method of Yen et al. (Arch. Int. Pharmacodyn. 123: 179-185, 1959) and Jannsen et al. (J. Pharmacol. Exp. Ther. 129: 471-475, 1960). Male Balb/c mice (Charles River) were used. After 2 weeks of isolation in plastic cages (11.5×5.75×6 in) the mice were selected for aggression by placing a normal group-housed mouse in the cage with the isolate for a maximum of 3 min. Isolated mice failing to consistently attack an intruder were eliminated from the colony.

Drug testing was carried out by treating the isolated mice with test drugs or standards. Fifteen min after dosing with drugs by the oral route (po), one isolated mouse was removed from its home cage and placed in the home cage of another isolate. Scoring was a yes or no response for each pair. A maximum of 3 min was allowed for an attack and the pair was separated immediately upon an attack. Selection of home cage and intruder mice was randomized for each test. Mice were treated and tested twice a week with at least a 2 day washout period between treatments.

As shown in Table II, haloperidol and Examples 68, 114, 134, 135, 136, 138 and 181 all have potent activities in inhibiting the isolation-induced aggressive behavior indicating psychotropic activities.

(+)-N-Allylncrmetazocine-Induced Turning Behavior in Rats

Male Sprague-Dawley rats (CD/CR, Charles River), weighing 190-290 g, were used for surgery. In order to spare nonadrenergic neurons, rats were injected with 25 mg/kg imipramine intraperitoneal (i.p.) 30 min before surgery. The rats were anesthetized with a 1:1.2 ratio mixture of Xylazine:Ketamine given 0.1 mL/100 g body weight intramuscular (i.m.). A Ringers-Wydaze (100:0.01) solution was given to prevent dehydration. Dopamine was depleted in the right striatum by injecting the neurotoxin 6-hydroxydopamine (6-OHDA) into the substantia nigra of the right cerebral hemisphere. Five mg of 6-OHDA was dissolved in 5 mL of a 0.04% ascorbic acid solution which had been deoxygenated with nitrogen. Five $\mu$L of the 6-OHDA solution was injected into the substantia nigra through a 26 gauge needle over a five min period. Stereotaxic injection coordinates were $-2.5$ mm posterior to bregma, $-2.1$ mm right of the midsagittal suture, and $-8.6$ mm below the skull surface with the incisor bar set at $+5.0$ mm. Following surgery they were given 10 days to recover while housed four per cage (45.0 L×20.0 H×26.0 W) with ALPHA-dri bedding and ad lib access to Pro-Lab rodent chow and deionized water. Following recovery, the wood clips were removed, the rats were individually housed in suspended cages, and they were placed on a restricted diet so that their weight did not exceed 375 g. At all times they were housed in the animal care facility under a 12-12 hour light/dark cycle (light on at 6:00 h, light off at 18:00 h).

Rotation rate and direction were determined with Coulbourn Instruments Rotometry Monitors. Clockwise and counterclockwise rotations were recorded at 30 and 60 min intervals. The rats were examined for correct lesion location by testing for rotational activity induced by subcutaneous (s.c.) injections of 3.0 mg/kg D-amphetamine S04, and 4.0 mg/kg (+)-N-allylnormetazocine [(+)-SKF 10,047], respectively. These drugs were administered in the following sequence: Amphetamine was given 30 sec before testing. Seven days later, the rats were injected with (+)-N-allylnormetazocine 30 sec before testing. Only those rats with an ipsilateral rotation rate of 2.5 turns per min or higher were used in subsequent tests.

Methocel ® or test drugs were administered p.o. 20 min before testing. (+)-N-allylnormetazocine (4.0 mg/kg) was given s.c. immediately before testing.

The data was analyzed with an analysis of variance statistical test, and individual comparisons of each dose of test drug to control were made with Dunnett's multiple range test. The ED50 was calculated with a Litchfield and Wilcoxon test using percent of control values. As shown in Table III, both haloperidol and Example 68 potently antagonized the sigma hallucinogen N-allylnormetazocine-induced rotation in this rat model. The hallucinogen PCP also has significant affinity for the sigma receptor (Tam, Eur. Pharmacol. 109: 33-41 (1985)).

TABLE I

| | In vitro Receptor Binding Affinities | |
|---|---|---|
| Example | Sigma | Dopamine (D-2) |
| Haloperidol | +++ | +++ |
| 181 | +++ | + |
| 68 | +++ | − |
| 134 | +++ | − |
| 181 | +++ | − |
| 182 | +++ | − |
| 198 | +++ | − |
| 199 | +++ | − |
| 135 | +++ | − |
| 183 | +++ | − |
| 192 | +++ | − |
| 205 | +++ | + |
| 193 | +++ | − |
| 194 | +++ | − |
| 309 | +++ | − |
| 200 | +++ | − |
| 84 | +++ | + |
| 81 | +++ | − |
| 69 | +++ | − |
| 126 | +++ | − |
| 114 | +++ | − |
| 136 | +++ | − |
| 137 | +++ | − |
| 115 | +++ | − |
| 203 | +++ | − |
| 195 | +++ | + |
| 187 | +++ | − |
| 196 | +++ | + |
| 188 | +++ | − |
| 197 | +++ | − |
| 185 | +++ | − |
| 189 | +++ | − |
| 186 | +++ | − |
| 190 | +++ | − |
| 138 | +++ | + |

TABLE II

| Example | In vivo Inhibition of Isolation-Induced Aggression |
|---|---|
| Haloperidol | +++ |
| 181 | ++ |
| 68 | +++ |
| 134 | +++ |
| 135 | ++ |
| 114 | +++ |
| 136 | + |

TABLE II-continued

| | In vivo |
|---|---|
| Example | Inhibition of Isolation-Induced Aggression |
| 138 | ++ |

TABLE III

| | In vivo |
|---|---|
| Example | Inhibition of (+)-N-Allylnor-metazocine-Induced Turning |
| Haloperidol | +++ |
| 68 | ++ |

Dosage Forms

Daily dosage ranges from about 1 mg to 2000 mg. Dosage forms (compositions) suitable for administration ordinarily will contain 0.5–95% by weight of the active ingredient based on the total weight of the composition.

The active ingredient can be administered orally in solid dosage forms, such as capsules, tablets, and powders, or in liquid dosage forms, such as elixirs, syrups, and suspensions; it can also be administered parenterally in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, 17th Ed. (1985) A. Osol, a standard reference text in this field.

Agricultural Utility

The compounds of this invention are useful as plant disease control agents. They are effective in controlling a broad spectrum of plant diseases, particularly foliar pathogens of ornamental, vegetable, field, cereal and fruit crops, such as *Puccinia recondita, Erysiphe cichoracearum, Erysiphe graminis, Venturia inaequaliz, Cercospora arachidicola, Monilinia fructicola, Phizoctonia solani, Pyriculari oryzae, Botrytis cinerea, Cercosporidium personatum, Podosphrera leucotrihca, Sclerotinia sclerotiorum, Cercospora beticola, Uncinula necatur, Septoria triticia and Septoria nodorum*. They also control seed pathogens.

Disease control is ordinarily accomplished by applying an effective amount of the compound either pre- or post-infection to the portion of the plant to be protected, such as the roots, stems, foliage, fruit, seeds, tubers or bulbs, or to the media (soil or sand) in which the plants to be protected are growing. The compound may also be applied to the seed from which the plants to be protected are to be grown.

Rates of application for these compounds can be influenced by many factors of the environment and should be determined under actual use conditions. Foliage can normally be protected when treated at a rate of from less than 1 g/ha to 5000 g/ha of active ingredient. Plants growing in soil treated at a concentration from 0.1 to about 20 kg/ha can be protected from disease. Seed and seedlings can normally be protected when seed is treated at a rate of from about 0.06 to about 3 grams per kilogram of seed.

The compounds of this invention can be mixed with fungicides, bactericides, acaricides, nematicides, insecticides, or other biologically active compounds in order to achieve desired results with a minimum expenditure of time, effort and material. Amounts of these biologically active materials added for each part by weight of the composition of this invention may vary from 0.05 to 25 parts by weight. Suitable agents of this type are well known to those skilled in the art. Some are listed below:

Fungicides methyl 2-benzimidazolecarbamate (carbendazim)
tetramethylthiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
2-cyano-N-ethylcarbamoyl-2-methoxyiminoacetamide (cymoxanil)
N-(trichloromethylthio)tetrahydrophthalimide (captan)
N-(trichloromethylthio)phthalimide (folpet)
dimethyl 4,4'-(o-phenylene)bis(3-thioallophanate)(thiophanate methyl)
2-(thiazol-4-yl)benzimidazole (thiabendazole)
aluminum tris (0-ethyl phosphonate)(phosethyl aluminum)
tetrachloroisophthalonitrile (chlorothalonil)
2,6-dichloro-4-nitroaniline (dichloran)
N-(2,6-dimethylphenyl)-N-(methoxyacetyl)alanine methyl ester (metalaxyl)
cis-N-[1,1,2,2-tetrachloroethyl)thio]cyclohex-4-ene-1,2-dicarbioximide (captafol)
3-(3,5-dichlorophenyl)-N-(1-methylethyl)-2,4-dioxo-1-imidazolidine carboxamide (iprodione)
3-(3,5-dichlorophenyl)-5-ethenyl-5-methyl-2,4-oxazolidinedione (vinclozolin)
kasugamycin
O-ethyl-S,S-diphenylphosphorodithioate(edifenphos)
4-(3-(4-(1,1-dimethylethyl)phenyl)-2-methyl)propyl2,6-dimethylmorpholine (Fenpropimorph)
4-(3,4(1,1-dimethylethylphenyl)-2-methyl)propylpiperidine (Fenpropidine)

1-[[(bis(4-fluorophenyl)methylsilyl]methyl]-1H-1,2,4-triazole (flusilazole)
2-p-chlorophenyl-2-(1H-1,2,4-triazol-1-ylmethyl)hexanenitrile (myclobutanil)
(±)-1-[2-(2,4-dichlorophenyl)-4-propyl-1,3-dioxolan2-ylmethyl]-1H-1,2,4-triazole (propiconazole)
N-propyl-N-[2-(2,4,6-trichlorophenoxy)ethyl-]imidazole1-carboxamide (prochloraz)
(RS)-2,4'-difluoro-α-(1H-1,2,4-triazol-1-ylmethyl)benzhydryl alcohol (flutriafol)
1-(4-chlorophenoxy)-3,3-dimethyl-1-(1H-1,2,4-triazol-1-yl)butanone (triadimefon)
1-(4-chlorophenoxy)-3,3-dimethyl-1-(1H-1,2,4-triazol-1-yl)butan-2-ol (triadimenol)
(2RS,3RS)-1-(2,4-dichlorophenyl)-4,4-dimethyl-2-(1H-1,2,4-triazol-1-yl) pentan-3-ol (dichlobutrazol)

Bactericides tribasic copper sulfate
streptomycin sulfate
oxytetracycline

Acaricides senecioic acid, ester with 2-sec-butyl-4,6-dinitrophenol (binapacryl)
6-methyl-1,3-dithiolo[2,3,B]quinonolin-2-one (oxythioquinox)
2,2,2-trichloro-1,1-bis(4-chlorophenyl)ethanol(dicofol)
bis(pentachloro-2,4-cyclopentadien-1-yl) (dienochlor)
tricyclohexyltin hydroxide (cyhexatin)
hexakis(2-methyl-2-phenylpropyl)distannoxane (fenbutin oxide)

Nematocides

2-[diethoxyphosphinylimino]1,3-diethietane (fosthietan)
S-methyl 1-(dimethylcarbamoyl)-N-(methylcarbamoyloxy)thioformimidate(oxamyl)
S-methyl 1-carbamoyl-N-(methylcarbamoyloxy)thioformimidate
N-isopropylphosphoramidic acid, O-ethyl O'-[4-(methylthio)-m-tolyl]diester (fenamiphos).

Insecticides:

3-hydroxy-N-methylcrotonamide(dimethylphosphate)ester (monocrotophos)
methylcarbamic acid, ester with 2,3-dihydro-2,2-dimethyl-7-benzofuranol (carbofuran)
O-[2,4,5-trichoro-α-(chloromethyl)benzyl]phosphoric acid, O',O'-dimethyl ester (tetrachlorvinphos)
2-mercaptosuccinic acid, diethyl ester, S-ester with thionophosphoric acid, dimethyl ester (malathion)
phosphorothioic acid, O,O-dimethyl, O-p-nitrophenyl ester (methyl parathion)
methylcarbamic acid, ester with α-naphthol (carbaryl)
methyl N-[[(methylamino)carbonyl]oxy]ethanimidothioate (methomyl)
N'-(4-chloro-o-tolyl)-N,N-dimethylformamidine (chlordimeform)
O,O-diethyl-O-(2-isopropyl)-4-methyl-6-pyrimidyl)-phosphorothioate (diazinon)
octachlorocamphene (toxaphene)
O-ethyl O-p-nitrophenyl phenylphosphonothioate (EPN)
cyano(3-phenoxyphenyl)-methyl-4-chloro-α-(1-methylethyl)benzeneacetate (fenvalerate)
(3-phenoxyphenyl)methyl(±)-cis,trans-3-(2,2-dichloroethenyl)-2,2-dimethylcyclopropanecarboxylate (permethrin)
dimethyl N,N'-[thiobis(N-methylimino)carbonyloxy]]-bis[ethanimidothioate] (thiodicarb)
phosphorothiolothionic acid, 0-ethyl-0-[4-(methylthio)-phenyl]-S-n-propyl ester (sulprofos)
α-cyano-3-phenoxybenzyl 3-(2,2-dichlorovinyl)-2,2-dimethylcyclopropane carboxylate (cypermethrin)
cyano(3-phenoxyphenyl)methyl 4-(difluoromethoxy)α-(methylethyl)benzeneacetate (flucythrinate)
O,O-diethyl-O-(3,5,6-trichloro-2-pyridyl)phosphorothioate (chlorpyrifos)
O,O-dimethyl-S-[[(4-oxo-1,2,3-benzotriazin-3-(4H)-yl)methyl]phosphorodithioate (azinphos-methyl)
5,6-dimethyl-2-dimethylamino-4-pyrimidinyl dimethyl carbamate (pirimicarb)
S-(N-formyl-N-methylcarbamoylmethyl)-O,O-dimethylphosphorodithioate (formothion)
S-2-(ethylthioethyl)-O,O-dimethyl phosphiorothioate (demeton-S-methyl)
α-cyano-3-phenoxybenzyl cis-3-(2,2-dibromovinyl)2,2-dimethylcyclopropane carboxylate (deltamethrin)
cyano(3-phenoxyphenyl)methyl ester of N-(2-chloro-4-trifluoromethylphenyl)alanine (fluvalinate)

The fungicidal properties of the subject compounds were discovered in a number of greenhouse tests. The test procedures and results follow:

Test A

The test compounds were dissolved in acetone in an amount equal to 6% of the final volume and then suspended at a concentration of from 1000 to 2 ppm in purified water containing 250 ppm of the surfactant TREM 014 (polyhydric alcohol esters). This suspension was sprayed to the point of run-off on wheat seedlings. The following day plants were inoculated with a spore dust of *Erysiphe graminis* f. sp. *tritici*, the causal agent of wheat powdery mildew, and incubated in a growth chamber at 20° C. for 7 days, when disease ratings were made.

Test B

The test compounds were dissolved in acetone in an amount equal to 6% of the final volume and then suspended at a concentration of from 1000 to 2 ppm in purified water containing 250 ppm of the surfactant TREM 014 (polyhydric alcohol esters). This suspension was sprayed to the point of run-off on wheat seedlings. The following day plants were inoculated with a spore suspension of *Puccinia recondita*, the causal agent of wheat leaf rust, and incubated in a saturated humidity chamber at 20° C. for 24 hours and then in a growth chamber at 20° C. for 8 days, when disease ratings were made.

Test C

The test compounds were dissolved in acetone in an amount equal to 6% of the final volume and then suspended at a concentration of from 1000 to 2 ppm in purified water containing 250 ppm of the surfactant TREM 014 (polyhydric alcohol esters). This suspension was sprayed to the point of run-off on apple seedlings. The following day plants were inoculated with a spore suspension of *Venturia inaequalis*, the causal agent of apple scab, and incubated in a saturated humidity chamber at 20° C. for 24 hours and then in a growth chamber at 22° C. for 11 days, when disease ratings were made.

Test D

The test compounds were dissolved in acetone in an amount equal to 6% of the final volume and then suspended at a concentration of from 1000 to 2 ppm in purified water containing 250 ppm of the surfactant TREM 014 (polyhydric alcohol esters). This suspension was sprayed to the point of run-off on peanut seedlings. The following day plants were inoculated with a spore suspension of Cercosporidum personatum, the causal agent of peanut late leaf spot, and incubated in a saturated humidity chamber at 22° C. for 24 hours and then in a high humidity chamber at 27° C. for 7 days, and then in a growth chamber at 29° C. for 7 days, when disease ratings were made.

Test E

The test compounds were dissolved in acetone in an amount equal to 6% of the final volume and then suspended at a concentration of from 1000 to 2 ppm in purified water containing 250 ppm of the surfactant TREM 014 (polyhydric alcohol esters). This suspension was sprayed to the point of run-off on cucumber seedlings. The following day plants were inoculated with a spore suspension of Botrytis cinerea, the causal agent of cucumber grey mold, and incubated in a saturated humidity chamber at 20° C. for 48 hours and then in a greenhouse for 5 days, when disease ratings were made.

Test F

The test compounds were dissolved in acetone in an amount equal to 6% of the final volume and then suspended at a concentration of from 1000 to 2 ppm in purified water containing 250 ppm of the surfactant TREM 014 (polyhydric alcohol esters). This suspension was sprayed to the point of run-off on tomato seedlings. The following day plants were inoculated with a spore suspension of Phytophthora infestans, the causal agent of tomato late blight, and incubated in a saturated humidity chamber at 20° C. for 24 hours and then in a growth chamber at 20° C. for 5 days, when disease ratings were made.

Test G

The test compounds were dissolved in acetone in an amount equal to 6% of the final volume and then suspended at a concentration of from 1000 to 2 ppm in purified water containing 250 ppm of the surfactant TREM 014 (polyhydric alcohol esters). This suspension was sprayed to the point of run-off on grape seedlings. The following day plants were inoculated with a spore suspension of Plasmopara viticola, the causal agent of grape downy mildew, and incubated in a dew chamber at 20° C. for 24 hours and then in a growth chamber a 20° C. for 7 days, when disease ratings were made.

Test H

The test compounds were dissolved in acetone in an amount equal to 6% of the final volume and then suspended at a concentration of from 1000 to 2 ppm in purified water containing 250 ppm of the surfactant TREM 014 (polyhydric alcohol esters). This suspension was sprayed to the point of run-off on rice seedlings. The following day plants were inoculated with a spore suspension of Pyricularia oryzae, the causal agent of rice blast, and incubated in a saturated humidity chamber at 27° C. for 24 hours and then in a growth chamber at 29° C. for 4 days, when disease ratings were made.

Test I

The test compounds were dissolved in acetone in an amount equal to 6% of the final volume and then suspended at a concentration of from 1000 to 2 ppm in purified water containing 250 ppm of the surfactant TREM 014 (polyhydric alcohol esters). This suspension was sprayed to the point of run-off on rice seedlings. The following day plants were inoculated with a mycelial suspension of Rhizoctonia solani, the causal agent of rice sheath blight, and incubated in a saturated humidity chamber at 27° C. for 48 hours and then in a growth chamber at 29° C. for 4 days, when disease ratings were made.

Results for Tests A–I are given in Table IV. In Table IV, a rating of 100 indicates 100% disease control and a rating of 0 indicates no disease control relative to untreated controls. A —entry indicates that no test was performed with the specific compound at that specific rate.

TABLE IV

| EX# | A | B | C | D | E | F | G | H | I |
|---|---|---|---|---|---|---|---|---|---|
| 195 | 99 | 73 | 68 | 46 | 0 | 0 | — | 0 | 0 |
| 187 | 98 | 96 | 51 | 0 | 0 | 0 | — | 0 | 0 |
| 196 | 0 | — | 90 | 0 | 0 | 26 | 40 | 0 | 0 |
| 188 | 100 | 72 | 93 | 82 | 18 | 8 | 89 | 0 | 0 |
| 185 | 29 | 0 | 28 | 26 | 0 | 0 | — | 0 | 0 |
| 312 | 97 | 27 | 16 | 51 | 0 | 0 | — | 0 | 0 |
| 189 | 99 | 26 | 86 | 75 | 0 | 0 | — | 0 | 0 |
| 186 | 0 | — | 81 | 0 | 0 | 0 | — | 0 | 0 |
| 181 | 87 | 37 | 55 | 82 | — | 0 | — | 0 | 0 |
| 182 | 63 | -27 | 0 | 0 | — | 0 | — | 0 | 0 |
| 205 | 94 | 35 | 66 | 30 | 33 | 0 | — | 0 | 0 |
| 313 | 97 | 29 | 40 | 91 | 0 | 0 | — | 0 | 0 |
| 314 | 91 | — | 46 | 75 | 8 | 0 | — | 0 | 39 |
| 315 | 99 | 52 | 90 | 46 | 0 | 0 | — | 0 | 19 |

Formulatins

The method of this invention can be conveniently carried out by formulating a compound of Formula (I) in the conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, boradly, contain about 0.1% to 99% by weight of active ingredient(s) and at least one of (a) about 0.1% to 2% surfactant(s) and (b) about 1% to 99.9% solid or liquid inert diluent(s). More specifically, they will contain these ingredients in the following approximate proportions:

| | Weight Percent* | | |
|---|---|---|---|
| | Active Ingredient | Diluent(s) | Surfactant(s) |
| Wettable Powders | 20–90 | 0–74 | 1–10 |
| Oil Suspensions. | 3–50 | 40–95 | 0–15 |
| Emulsions, Solutions, (including Emulsifiable Concentrates) | | | |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength | 90–99 | 0–10 | 0–2 |

-continued

| | Weight Percent* | | |
|---|---|---|---|
| Compositions | Active Ingredient | Diluent(s) | Surfactant(s) |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carrier", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, N.Y., 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering", Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138-140, 162-164, 166, 167 and 169-182;

H. Gysin and E. Knusli, U.S. Pat. No. 2,891,855, Jun. 23, 1959, Col. 3, line 66 through Col. 5, line 17 and Examples 1-4;

G. C. Klingman, "Weed Control as a Science", John Wiley and Sons, Inc. New York, 1961, pp. 81-96; and J. D. Fryer and S. A. Evans, "Weed control Handbook", 5th Ed., Blackwell Scientifica Publications, Oxford, 1968, pp. 101-103.

What is claimed is:

1. A method of treating physiologic or drug-induced psychosis or dyskinesia in a mammal comprising administering to the mammal an effective amount of a compound of the formula:

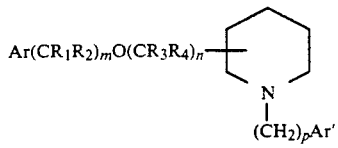

or a pharmaceutically acceptable salt thereof wherein:

$R_1$ to $R_4$ independently are H, alkyl of 1 to 3 carbon atoms or $AR''$;

Ar, Ar' and Ar'' independently are phenyl groups optionally substituted with 1 to 5 substituents independently selected from the group consisting of:
H, halogen, OH, alkoxy of 1 to 4 carbon atoms, $NR_5R_6$, SH, $(SO)_qR_7$ where $q=0$, 1 or 2, haloalkyl of 1 to 3 carbon atoms and 1 to 7 halogen atoms, alkyl of 1 to 4 carbon atoms, $CO_2H$, carboalkoxy of 2 to 6 carbon atoms, $CONR_8R_9$, CN, $NO_2$, $SO_2NR_{10}R_{11}$, $SO_3H$ or $OSiR_{12}R_{13}R_{14}$; or Ar and Ar' independently are naphthyl, each optionally substituted with 1 to 5 substituents independently selected from the group consisting of:
H, halogen, OH, alkoxy of 1 to 4 carbon atoms, $NR_5R_6$, SH, $S(O)_qR_7$ where $q=0,1,2$, haloalkyl of 1 to 3 carbon atoms and 1 to 7 halogen atoms, alkyl of 1 to 4 carbon atoms, $CO_2H$, carboalkoxy of 2 to 6 carbon atoms, $CONR_8R_9$, CN, $NO_2$, $SO_2NR_{10}R_{11}$, $SO_3H$ or $OSiR_{12}R_{13}R_{14}$;

$R_5$-$R_{14}$ independently are H or alkyl of 1 to 4 carbon atoms;

m is 0 to 5;

n is 0 to 5 provided however that m and n cannot both be 0; and p is 1 or 2.

2. A method of claim 1 wherein $m=n \leq 3$.

3. A method of claim 1 wherein p is 1.

4. A method of claim 1 wherein $R_1$ to $R_4$ are H.

5. A method of claim 1 wherein
$m+n \leq 3$;
p is 1;
$R_1$ to $R_4$ are H; and
Ar and Ar' independently are naphthyl, or phenyl each optionally substituted with 1 to 3 substituents independently selected from the group consisting of:
H, halogen, OH, alkoxy of 1 to 4 carbon atoms, $NR_5R_6$, SH, $(SO)_qR_7$ where $q=1$, 2 or 2, haloalkyl of 1 to 3 carbon atoms and 1 to 7 halogen atoms, alkyl of 1 to 4 carbon atoms, $CO_2H$, carboalkoxy of 2 to 6 carbon atoms, $CONR_8R_9CN$, $NO_2SO_2NR_{10}R_{11}$, $SO_3H$ or $OSiR_{12}R_{13}R_{14}$.

6. A method of claim 5 wherein the compound is 1-benzyl-4-(2'(4''-fluorophenoxy)ethyl)piperidine, or the hydrochloride salt thereof.

7. A method of claim 5 wherein the compound is 1-benzyl-4-(4'-fluorophenoxymethyl)piperidine, or the hydrochloride salt thereof.

8. A method of claim 5 wherein the compound is 1-benzyl-4-(4'-chlorophenoxymethyl)piperidine, or the hydrochloride salt thereof.

9. A method of claim 5 wherein the compound is 1-(4,-fluorobenzyl)-4-(4''-fluorophenoxymethyl)-piperidine.

10. A method of claim 5 wherein the compound is 1-(2'-naphthylmethyl)-4-(4'''-fluorophenoxymethyl)-piperidine.

11. A method of claim 5 wherein the compound is 1-benzyl-4-(4'-trifluoromethyl)phenoxymethyl)piperidine, or the hydrochloride salt thereof.

12. A method of claim 5 wherein the compound is 1-(4'-methoxybenzyl)-4-(4'fluorophenoxymethyl)-piperidine, or the maleate salt thereof.

13. A method of claim 5 wherein the compound is 1-(4'-chlorobenzyl)-4-(4'-fluorophenoxymethyl)piperidine, or the hydrochloride salt thereof.

14. A method of claim 5 wherein the compound is 1-phenethyl-4-(4'-fluorobenzyloxymethyl)piperidine, or the hydrochloride salt thereof.

15. A method of claim 5 wherein the compound is 1-phenethyl-4-(4-'-fluorobenzyloxymethyl)piperidine, or the maleate salt thereof.

16. A method of claim 5 wherein the compound is 1-(1'-naphthylamethyl)4-(4''-fluorobenzyloxymethyl)-piperidine, or the hydrochloride salt thereof.

17. A compound selected from the group consisting of
(1-benzyl-4-(2'(4''-fluorophenoxy)ethyl)piperidine, or the hydrochloride salt thereof;
1-benzyl-4-(440 -fluorophenoxymethyl)piperidine, or the hydrocholoride salt thereof;
1-benzyl-4-(4'-chlorophenoxymethyl)piperidine, or the hydrochloride salt thereof;
1-(2'-naphthylmethyl)-4-(4'-fluorophenoxymethyl) piperidine;
1-benzyl-4-(4'-trifluoromethyl) phenoxymethyl)-piperidine, or the hydrocloride salt thereof;
1-(4'-chlorobenzyl)-4-(4'-fluorophenoxymethyl)-piperidine, or the hydrochloride salt thereof;
1-benzyl-(4'-nitrophenoxymethyl)piperidine, or the hydrochloride salt thereof;
1-(1'-naphthylmethyl)-4-(4''-fluorobenzyloxymethyl)-piperidine, or the hydrochloride salt thereof; and
(4-[[4-[[(4-fluorophenyl)methoxy]methyl]-1-piperidinyl]-methyl]phenol, or the hydrochloride salt thereof.

18. A compound selected from the group consisting essentially of
(1-(4'-fluorobenzyl)-4-(4''-fluorophenoxymethyl)-piperidine;
1-[(4-chlorophenyl)methyl]-4-[[4-fluorophenyl)methoxy]-methyl]-piperidine; and
1-[(4-cyclohexyl)methyl]-4-[[(4-fluorophenyl)methoxy]methyl]-piperidine.

19. A compound selected from the group consisting essentially of
1-(4'-methoxybenzyl)-4-(4-fluorophenoxymethyl)-piperidine, or the maleate salt thereof; and
1-phenethyl-4-(4'-fluorobenzyloxymethyl)piperidine, or the maleate salt thereof.

20. A pharmaceutical composition comprising a pharmaceutically acceptable carrier and an antipsychotic or antidyskinetic effective amount of a compound selected from the group consisting essentially of
1-benzyl-4-(2'(4''-fluorophenoxy)ethyl)piperidine, or the hydrochloride salt thereof;
1-benzyl-4-(4'-fluorophenoxymethyl)piperidine, or the hydrochloride salt thereof;
1-benzyl-4-(4'-chlorophenoxymethyl)piperidine, or the hydrochloride salt thereof;
1-(4'-fluorobenzyl)-4-(4''-fluorophenoxymethyl) piperidine;
1-(2-naphthylmethyl)-4-(4''-fluorophenoxymethyl) piperidine;
1-benzyl-4-(4'-trifluoromethyl) (phenoxymethyl) piperidine, or the hydrochloride salt thereof;
1-(4'-methoxybenzyl)-4-(4'-fluorophenoxymethyl) piperidine, or the maleate salt thereof;
1-(4'-chlorobenzyl)-4-(4'-chlorobenzyl)-4-(4'-fluorophenoxymethyl)piperidine, or the hydrochloride salt thereof;
1-benzyl-(4'-nitrophenoxymethyl)piperidine, or the hydrochloride salt thereof;
1-phenethyl-4-(4'-fluorobenzyloxymethyl)piperidine, or the maleate salt thereof; and
1-(1'-naphthylmethyl)-4-(4''-fluorobenzyloxymethyl)-piperidine, or the hydrochloride salt thereof.

21. A composition for controlling fungal disease in plants which comprises an effective amount of a compound selected from the group consisting essentially of
1-[(4-chlorophenyl)methyl]-4-[[(4-fluorophenyl)methoxy]-methyl]-piperidine;
1-[(cyclohexyl)methyl]4-[[(4-fluorophenyl)methoxy]-methyl]-piperidine; and
4-[(4-fluorophenyl)methoxy]methyl]-1-piperidinyl]-methylphenol, or the hydrochloride salt thereof.

* * * * *